(12) United States Patent
Clokie

(10) Patent No.: US 10,286,019 B2
(45) Date of Patent: May 14, 2019

(54) THERAPEUTIC BACTERIOPHAGES

(71) Applicant: University of Leicester, Leicester (GB)

(72) Inventor: Martha Clokie, Leicester (GB)

(73) Assignee: University of Leicester, Leicester (GB)

( * ) Notice: Subject to any disclaimer, the term of this patent is extended or adjusted under 35 U.S.C. 154(b) by 88 days.

(21) Appl. No.: 14/423,284

(22) PCT Filed: Aug. 27, 2013

(86) PCT No.: PCT/GB2013/052245
§ 371 (c)(1),
(2) Date: Feb. 23, 2015

(87) PCT Pub. No.: WO2014/030020
PCT Pub. Date: Feb. 27, 2014

(65) Prior Publication Data
US 2015/0290263 A1    Oct. 15, 2015

(30) Foreign Application Priority Data

Aug. 24, 2012   (GB) .................................. 1215184.1

(51) Int. Cl.
*A61K 35/76*   (2015.01)
*C12N 7/00*   (2006.01)

(52) U.S. Cl.
CPC .............. *A61K 35/76* (2013.01); *C12N 7/00* (2013.01); *C12N 2795/00032* (2013.01)

(58) Field of Classification Search
CPC ................................ A61K 35/76; C12N 7/00
USPC ......................................... 424/93.6
See application file for complete search history.

(56) References Cited

U.S. PATENT DOCUMENTS

2010/0297086 A1   11/2010   Mathers et al.
2010/0310522 A1   12/2010   Gasson et al.

OTHER PUBLICATIONS

Horgan et al. "Genome analysis of the Clostridium difficile phage CD6356, a temperate phage of the Siphoviridae family" Gene, vol. 462: 34-43.*
Govind et al., "In vivo lysogenization of a *Clostridium difficile* bacteriophage φCD119," *Anaerobe* (2011) 17:125-129.
Housby et al., "Phage therapy," *Drug Discovery Today* (Jun. 2009), 14(11/12):536-540.
International Search Report dated Oct. 9, 2013 for International Application No. PCT/GB2013/052245.
Kandasamy et al, "The Use of Phage Therapy to treat *Clostridium difficile* Disease in Hamsters," *Abstracts of the 101st General Meeting of the American Society for Microbiology* (2001), 1001:474-475.
Meader et al., "Bacteriophage treatment significantly reduces viable *Clostridium difficile* and prevents toxin production in an in vitro model system," *Anaerobe* (2010), 16:549-554.
Nale et al., "Diverse Temperate Bacteriophage Carriage in *Clostridium difficile* 027 Strains," *PLoS ONE* (May 2012), 7(5):e372631-9.
Ramesh et al., "Prevention of *Clostridium difficile*-induced ileocecitis with Bacteriophage," *Anaerobe* (1999), 5:69-78.

* cited by examiner

*Primary Examiner* — Louise W Humphrey
*Assistant Examiner* — Teresa E Knight
(74) *Attorney, Agent, or Firm* — Pepper Hamilton LLP

(57) ABSTRACT

The present invention relates to a panel of bacteriophage, wherein the panel comprise any one or more bacteriophage selected from the group consisting of:—NCTC 12081404, NCTC 12081405, NCTC 12081406, NCTC 12081407, NCTC 12081408, NCTC 12081409 and NCTC 12081410. The invention also relates to the use of such panels for treating *C. difficile* infection, or for prophylactic treatment of subjects not yet colonized by *C. difficile* or that have been colonized but the colonization has not yet progressed to infection.

8 Claims, 15 Drawing Sheets

THERAPEUTIC BACTERIOPHAGES

The present invention relates to panels of bacteriophages and to pharmaceutical compositions, in particular, but not exclusively, such panels are for use in treating *Clostridium difficile* infection, or prophylactic treatment where the subject to be treated has not yet been colonised by *C. difficile*, or a subject that has been colonised by *C. difficile* but the colonisation has not progressed to infection.

*Clostridium difficile* (also referred to as *C. diff* or *C. difficile*) is a spore-forming Gram-positive anaerobic pathogenic bacterium that causes diarrhoea and colitis and can lead to death. Although this bacterium can be present in the gut of asymptomatic individuals, in other individuals the presence of *C. diff* may cause *Clostridium difficile* Associated Diarrhoea (CDAD). Additionally, asymptomatic individuals may develop CDAD after administration of broad-spectrum antibiotics. CDAD is a major healthcare and financial burden to the NHS and is also known as *Clostridium difficile* Infection (CDI).

Routinely, two small molecule antibiotics are used to treat *C. difficile* infections (metronidazole and vancomycin); resistance is developing to both. Consequently, new antimicrobials are desperately needed.

*C. difficile* strains are classified by "ribotyping". Ribotyping involves an analysis of the size and number of copies of ribosomal RNA genes, which establishes a genetic profile for each strain (known as ribotype). About 350 ribotypes are currently recognised. The standard protocol for ribotyping uses both PCR ribotyping coupled with agarose gel electrophoresis, or capillary analysis following the incorporation of a fluorescent primer.

Bacteriophages (also called phages) are viruses that specifically infect bacteria. Phages are thought to exist for all bacteria and they infect either single bacterial species, or sub-sets of strains within a species. They have been used successfully to treat bacterial infections for nearly a century, but their usage largely fell out of favour after the development of small molecule antibiotics in the 1940s. This was because small molecule antibiotics are effective against a greater range of bacterial species and so can be used in the absence of identification of the cause of the infection. The renewed interest in phages as a therapeutic has been motivated by problems associated with antibiotic resistance and the lack of new small molecule antibiotics being developed. Phage-based therapies offer a specific targeted weapon to be used against problematic bacterial species; they lack problems associated with dysbiosis, and resistance to them is typically slower to develop than to conventional small molecule antibiotics.

Significant challenges exist when attempting to identify suitable phage-based therapies. In particular, isolation and characterisation of phages is difficult. Even once a phage has been isolated and identified, the phage will only have therapeutic value if it possesses specific characteristics e.g. being both able to kill bacteria but also non-toxic to the animal being treated by the therapy.

The isolation and propagation of *C. difficile* bacteriophages (i.e. bacteriophages that infect *C. difficile*) is a particularly difficult process, as the organism is an obligate anaerobe that does not readily produce lawns suitable for observing bacteriophages. Until the research that is the subject of this specification, a total of only 5 *C. difficile* phages had been isolated; this is despite the efforts of at least four independent research groups. These five known phages were all isolated from clinical samples and the ribotype specificity of the phages has not been characterised in any detail.

The paucity of *C. difficile* phages that have been identified to-date has meant that work using phage to treat *C. difficile* infections has been more limited than for other bacterial species.

The inventors have, following extensive experimentation, identified 7 new bacteriophages, each of which have been isolated from environmental soil samples and their ribotype specificity characterised. All 7 new bacteriophages are capable of killing *Clostridium difficile*.

Accordingly, in a first aspect of the present invention, there is provided a panel of bacteriophage, wherein the panel comprise or consists of any one or more bacteriophage selected from the group consisting of: NCTC 12081404, NCTC 12081405, NCTC 12081406, NCTC 12081408, NCTC 12081409, NCTC 12081410 and NCTC 12081407. Each novel strain of bacteriophage has been deposited at the National Collection of Type Cultures (NCTC) under the Budapest Treaty, and each strain is accessible to the public per request. Accession number NCTC 12081404, *Clostridium difficile* phage CD-HS1 (infects CD105LC1), was deposited with the Health Protection Agency, Culture Collections, Portion Down, Salisbury SP4 0JG, United Kingdom, on Aug. 14, 2012. Accession number NCTC 12081405, *Clostridium difficile* phage CD-HM6 (infects CD105HE1), was deposited with the Health Protection Agency, Culture Collections, Portion Down, Salisbury SP4 0JG, United Kingdom, on Aug. 14, 2012. Accession number NCTC 12081406, *Clostridium difficile* phage CD-HM5 (infects CD105HE1), was deposited with the Health Protection Agency, Culture Collections, Portion Down, Salisbury SP4 0JG, United Kingdom, on Aug. 14, 2012. Accession number NCTC 12081407, *Clostridium difficile* phage CD-HM4 (infects CD105HS1), was deposited with the Health Protection Agency, Culture Collections, Portion Down, Salisbury SP4 0JG, United Kingdom, on Aug. 14, 2012. Accession number NCTC 12081408, *Clostridium difficile* phage CD-HM3 (infects CD105HE1), was deposited with the Health Protection Agency, Culture Collections, Portion Down, Salisbury SP4 0JG, United Kingdom, on Aug. 14, 2012. Accession number NCTC 12081409, *Clostridium difficile* phage CD-HM2 (infects CD105HE1), was deposited with the Health Protection Agency, Culture Collections, Portion Down, Salisbury SP4 0JG, United Kingdom, on Aug. 14, 2012. Accession number NCTC 12081410, *Clostridium difficile* phage CD-HM1 (infects CD105HE1), was deposited with the Health Protection Agency, Culture Collections, Portion Down, Salisbury SP4 0JG, United Kingdom, on Aug. 14, 2012.

Each of the phages recited above was deposited on 14 Aug. 2012 under the Budapest Treaty with the National Collection of Type Cultures (NCTC, UK). The depository numbers issued by the NCTC for each of the phages are recited above.

NCTC 12081404 is also referred to herein as CD-HS1.
NCTC 12081405 is also referred to herein as CD-HM6.
NCTC 12081406 is also referred to herein as CD-HM5.
NCTC 12081407 is also referred to herein as CD-HM4.
NCTC 12081408 is also referred to herein as CD-HM3.
NCTC 12081409 is also referred to herein as CD-HM2.
NCTC 12081410 is also referred to herein as CD-HM1.

The term panel of bacteriophage would be understood by the skilled person to be synonymous with the term preparation of isolated bacteriophage. The use of the term isolate requires that the phages of the present invention have been isolated and/or purified from their natural environment.

Such panels can include any one, or any combination, of the phages provided herein. When more than one phage is included in the panel, the phages may be prepared for separate, sequential or simultaneous administration. All combinations of bacteriophages that can be selected from the above recited group are contemplated individually for inclusion in the panels of this invention. For example, the panel may comprise or consist of all of NCTC 12081404, NCTC 12081405, NCTC 12081406, NCTC 12081407, NCTC 12081408, NCTC 12081409 and NCTC 12081410. The panel may comprise or consist of NCTC 12081404 and NCTC 12081408, optionally further comprising or consisting of NCTC 12081409 and/or NCTC 12081410. The panel may comprise or consist of NCTC 12081404.

Alternatively, or additionally, the panels according to the present invention that comprise or consist of the aforementioned phage, can have additional components; components that may not be phage. For example, carriers, excipients, therapeutic agents (eg non-phage agents, such as antibiotics). The use of the term "consists" can therefore mean that the panels include the recited phage(s) as the only phage(s) of the panel, but may include additional non-phage components.

Each phage was found to be capable of lysing *C. difficile* and has been further characterised.

The bacteriophages for inclusion in the panels of the present invention may include mutants and variants of the deposited bacteriophages defined above. Consequently, reference to any of NCTC 12081404, NCTC 12081405, NCTC 12081406, NCTC 12081408, NCTC 12081409, NCTC 12081410 and NCTC 12081407, includes reference to mutants or variants thereof. Such mutants and variants of the deposited bacteriophages retain the ability to kill *C. difficile*. The mutants and variants have at least 85%, at least 90%, at least 95%, at least 97%, at least 98% or at least 99% nucleotide sequence identity across the whole genome compared to the genome of at least any one of the deposited bacteriophages of the present invention. Such mutants and variants may result from additions, deletions or substitutions of nucleotides from the nucleic acid sequences of the deposited bacteriophages (for example the addition, deletion of substitution of 1, 2, 3, 4 or 5 nucleotides, optionally contiguous nucleotides). Optionally, the mutant or variant does not include an integrase gene and/or a toxin gene. In addition to retaining the ability to kill *C. difficile*, the mutant and variant may possess any further characteristic mentioned below for the deposited bacteriophage from which it is derived (eg. morphology, host specificity, genome length).

Optionally, the panel may comprise 2 or more different bacteriophages, 3 or more different bacteriophages, 4 or more different bacteriophages, 5 or more different bacteriophages, 6 or more different bacteriophages or 7 different bacteriophages.

The panel may be capable of killing more than 5, more than 10, more than 15, more than 20, more than 25, more than 30 or 32 different ribotypes of *C. difficile*. Optionally, at least 1 of the ribotypes will be 027 and/or 014/020.

As the skilled person would understand, the choice of phage or combination of phages, for inclusion in the panel of the present invention is determined by the ribotype(s) of *C. difficile* that is (are) intended to be killed by the panel.

For example, the panel according to the present invention may comprise or consist of NCTC 12081404. Such a panel has been found to be useful in treating infection from *C. difficile* ribotype 001 (e.g. in the UK and in Australia), ribotype 027 (e.g. in the US), ribotype 081 (e.g. in the UK), and/or ribotype 107 (e.g. in the UK).

The panel according to the present invention may comprise or consist of NCTC12081410 and/or NCTC12081409. Such panel has been found useful in treating infection from *C. difficile* ribotype No. 002, (e.g. in the UK), and/or ribotype 003 (e.g. in the UK).

The panel according to the present invention may comprise or consist of NCTC12081410, NCTC12081409 and/or NCTC12081408. Such panels have been found useful in treating infection from *C. difficile* ribotype No. 002, (e.g. in Australia), and/or ribotype 018 (e.g. in the UK).

The panel according to the present invention may comprise or consist of NCTC12081408, NCTC12081405 and/or NCTC12081406. Such a panel has been found useful in treating infection from *C. difficile* ribotype No. 013, (e.g. in the UK).

The panel according to the present invention may comprise or consist of NCTC12081410, NCTC12081409, NCTC12081408, NCTC12081405 and/or NCTC12081406. Such a panel has been found useful in treating infection from *C. difficile* ribotype No. 014/020, (e.g. in the UK).

The panel according to the present invention may comprise or consist of NCTC12081408 and/or NCTC12081405. Such a panel has been found useful in treating infection from *C. difficile* ribotype No. 014/020, (e.g. in the UK).

The panel according to the present invention may comprise or consist of NCTC12081408, NCTC12081404, NCTC12081406 and/or NCTC12081405. Such a panel has been found useful in treating infection from *C. difficile* ribotype No. 015, (e.g. in the UK).

The panel according to the present invention may comprise or consist of NCTC12081410, NCTC12081408, NCTC12081406 and/or NCTC12081405. Such a panel has been found useful in treating infection from *C. difficile* ribotype No. 023, (e.g. in the UK).

The panel according to the present invention may comprise or consist of NCTC12081406. Such a panel has been found useful in treating infection from *C. difficile* ribotype No. 026, (e.g. in the UK).

The panel according to the present invention may comprise or consist of NCTC12081408 and NCTC12081404. Such a panel has been found useful in treating infection from *C. difficile* ribotype No. 027, (e.g. in the UK).

The panel according to the present invention may comprise or consist of NCTC12081408, NCTC12081407 and/or NCTC12081404. Such a panel has been found useful in treating infection from *C. difficile* ribotype No. 087, (e.g. in the UK).

The panel according to the present invention may comprise or consist of NCTC12081410, NCTC12081408, NCTC12081409 and/or NCTC12081405. Such a panel has been found useful in treating infection from *C. difficile* ribotype No. 106, (e.g. in the UK).

In order to provide a panel that is capable of killing specific ribotypes of *C. difficile* irrespective of their origin, it may be advantageous to provide panels with combinations of phage best suited to treat *C. difficile* infections irrespective of their origin.

For example, in order to treat *C. difficile* ribotype 002 and/or 018 infection the panel according to the present invention may comprise or consist of NCTC12081410, NCTC12081409 and/or NCTC12081408.

In order to treat ribotype 003 infection the panel of the present invention may comprise or consist of NCTC12081410 and/or NCTC12081409.

In order to treat ribotype 013 infection the panel of the present invention may comprise or consist of NCTC12081408, NCTC12081405 and/or NCTC12081406.

In order to treat ribotype 014/020 infection the panel of the present invention may comprise or consist of NCTC12081410, NCTC12081409, NCTC12081408, NCTC12081406 and/or NCTC12081405.

In order to treat ribotype 015 infection the panel of the present invention may comprise or consist of NCTC12081408, NCTC12081404, NCTC12081406 and/or NCTC12081405.

In order to treat ribotype 023 infection the panel of the present invention may comprise or consist of NCTC12081410, NCTC12081408, NCTC12081406 and/or NCTC12081405.

In order to treat ribotype 027 infection the panel of the present invention may comprise or consist of NCTC12081408 and/or NCTC12081404.

In order to treat ribotype 087 infection the panel of the present invention may comprise or consist of NCTC12081408, NCTC12081407 and/or NCTC12081404.

In order to treat ribotype 106 infection the panel of the present invention may comprise or consist of NCTC12081410, NCTC12081408, NCTC12081409, and/or NCTC12081405.

Of course, in many situations one will not know the specific ribotype of the *C. difficile* infection to be treated. For example, it may be important to treat a *C. difficile* infection in a hospital as quickly as possible, without waiting for diagnostic results to accurately identify the ribotype of the strain of *C. difficile* predominating. In such a situation, it is important to provide a combination of bacteriophages that provides a *C. difficile* host specificity that covers the most likely range of ribotypes to be prevalent in that situation. For example, the panel according to the present invention may comprise or consist of NCTC12081410, NCTC12081408, NCTC12081405 or NCTC12081404.

Taking into account the specific ribotypes that are more prevalent in the UK and in Australia, a combination that may be most effective in the UK and Australia and that forms part of the present invention is a panel comprising or consisting of NCTC12081410, NCTC12081408 and/or NCTC12081404.

Taking into account the specific ribotypes that are more prevalent in the US, a combination that may be most effective in the US and that forms part of the present invention is a panel comprising or consisting of NCTC12081408 and/or NCTC12081404.

The phages may be associated with any one or more of the following characteristics:—
NCTC 12081404 (CD-HS1):—
Morphology corresponding to the features of FIG. 1G; a member of Siphoviridae; capable of infecting and lysing any one or more *C. difficile* ribotypes selected from the group consisting of: 010, 002, 005, 013, 014/020, 046, 001, 015, 026, 027, 050, 087, 106, 107, 031, 220 and/or; a genome length of about 40 kbp (+/−10%).
NCTC 12081405 (CD-HM6):—
Morphology corresponding to the features of FIG. 1F; a member of Myoviridae; capable of infecting and lysing any one or more *C. difficile* ribotypes selected from the group consisting of:— 010, 002, 014, 020, 026, 087, 220, 076, and/or; a genome length of about 50 kbp (+/−10%).
NCTC 12081406 (CD-HM5):—
Morphology corresponding to the features of FIG. 1E; a member of Myoviridae; capable of infecting and lysing any one or more *C. difficile* ribotypes selected from groups consisting of:— 010, 014/020, 015, 026, 027, 087, 220 and 076 and/or, a genome length of about 50 kbp (+/−10%).
NCTC 12081407 (CD-HM4):—
Morphology corresponding to the features of FIG. 1D; a member of Myoviridae; capable of infecting and lysing any one or more *C. difficile* ribotypes selected from the group consisting of:— 012, and 031, and/or; a genome length of about 50 kbp (+/−10%).
NCTC 12081408 (CD-HM3):—
Morphology corresponding to the features of FIG. 1C; a member of Myoviridae; capable of infecting and lysing one or more *C. difficile* ribotypes selected from the group consisting of: 002, 005, 013, 014/020, 015, 023, 026, 027, 078, 087, 031, 220 and 076 and/or; a genome length of about 50 kbp (+/−10%).
NCTC 12081409 (CD-HM2):—
Morphology corresponding to the features of FIG. 1B; a member of Myoviridae; capable of infecting and lysing one or more *C. difficile* ribotypes selected from the group consisting of:— 010, 002, 014/020, 015, 012, 220 and 076 and/or; a genome length of about 50 kbp (+/−10%).
NCTC 12081410 (CD-HM1):—
Morphology corresponding to the features of FIG. 1A; a member of Myoviridae; capable of infecting and lysing one or more *C. difficile* ribotypes selected from the group consisting of:— 010, 002, 013, 014/020, 026, 087, 220 and 076 and/or; a genome length of about 50 kbp (+/−10%).

The skilled person would be aware of the variety of *C. difficile* hosts that may be used to propagate the phage of the present invention. By way of example, the propagating host for the phages of the present invention may be selected from any one or more of HPA No 12081401, HPA No 12081402 or HPA No. 12081403. Optionally, NCTC 12081410, NCTC 12081409, NCTC 12081408, NCTC 12081406 and NCTC 12081405 are all propagated on HPA No 12081401. Optionally, NCTC 12081407 is propagated on HPA No 12081402. Optionally, NCTC 12081404 is propagated on HPA No 12081402.

To optimise a phage therapeutic for human use requires a well-characterised phage set or phage panel with an appropriate host range and the production of a robust stable product. This has never been achieved to-date for *C. difficile*. However, the inventors have, following extensive experimentation, identified that panels of the phages discussed above are able to kill a broad host range of *C. difficile* ribotypes.

Consequently, in a second aspect of the present invention, there is provided a panel comprising a plurality of bacteriophages and that is capable of killing more than 5 separate ribotypes of *C. difficile*.

Optionally, the panel may comprise 2 or more different bacteriophages, 3 or more different bacteriophages, 4 or more different bacteriophages, 5 or more different bacteriophages, 6 or more different bacteriophage or 7 different bacterionphages.

The panel may be capable of killing more than 10, more than 15, more than 20, more than 25, more than 30 or 32 different ribotypes of *C. difficile*. Optionally, at least 1 of the ribotypes will be 027 and/or 014/020.

The bacteriophages may be any one or more selected from the group described in the first aspect of the present invention.

Mutants and variants of the bacteriophages of the first and second aspects of the present invention that are capable of killing *C. difficile* form part of the present invention. Consequently, in a third aspect of the present invention, there is provided a panel comprising or consisting of one or more mutant or variant of any one or more of the bacteriophage recited above. Such mutants or variants are capable of lysing *C. difficile*.

The panel of the present invention has demonstrated therapeutic utility both in vitro and in vivo. Consequently, in a fourth aspect of the present invention, there is provided a pharmaceutical composition comprising any of the panels of the first, second or third aspects of the present invention. The composition may include pharmaceutically acceptable excipients and/or carriers. The composition may include an enteric coating around the panels in order to ensure release of phage into the gastrointestinal tract past the stomach. The composition may be prepared as a yoghurt drink and so may additionally include yoghurt.

The composition may be prepared for oral or rectal administration.

In a fifth aspect of the present invention, there is provided a composition comprising or consisting of any of the panels or compositions of the present invention for use in a method of treatment. The method of treatment may be the treatment of a *C. difficile* infection (ie the treatment of a subject in which a colonisation by *C. difficile* has resulted in disorders associated with such infection; eg including but not limited to diarrhea, colitis, sepsis, toxic megacolon, hypotension, or gastroenteral perforation, *C. difficile* associated disease). The method of treatment may however be a prophylactic method, and so used to treat a subject that has not yet been colonised by *C. difficile*, or where the subject has been colonised by *C. difficile* but that colonisation has not yet progressed to infection. Consequently, methods of treatment may include methods that involve the administration of the composition to an individual already infected with *C. difficile* and/or prophylactic methods (e.g. when the composition is administered to an individual not suffering from *C. difficile* infection, or prior to the administration of antibiotics).

The treatment may be the treatment of a *C. difficile* infection, which could be a gastroenteral or diarrheal infection. The treatment may be the treatment of CDAD (also known as CDI).

Consequently, in a sixth aspect of the present invention, there is provided a method of treating *C. difficile* infection comprising the steps of administering a therapeutically effective amount of any of the panels or compositions of the present invention to the subject to be treated. The subject may be any mammal, for example a human or pig.

The panels of the present invention are also useful in nutritional compositions, pet food products and/or supplements for treating or preventing *C. difficile* infection in those ingesting such products. Consequently, in a further aspect of the present invention, there is provided a nutritional composition, a pet food product and/or a supplement comprising a panel or composition of the present invention.

The present invention will now be described, by way of example, with reference to the accompanying figures, in which:—

FIG. 1 shows transmission electron micrograph (TEM) images of the seven phages of the present invention. The scale bar provided in each image represents a length of 100 nm. FIG. 1A is an image of CD-HM1 phage. FIG. 1B is an image of CD-HM2 phage. FIG. 1C is an image of CD-HM3 phage. FIG. 1D is an image of CD-HM4 phage. FIG. 1E is an image of CD-HM5 phage. FIG. 1F is an image of CD-HM6 phage. FIG. 1G is an image of CD-HS1 phage.

FIG. 2 shows the results of the *C. difficile* bacterial and spore count from the lumen associated gut wash and tissue of 5 hamsters (C1, C2, T1, T2, T3). T1 to T3 receiving phage treatment; C1 and C2 receiving no phage treatment. Abbreviations: Cae=Caecum, Col=Colon, TA=Tissue associated, LA=Lumen associated.

Figure 1:
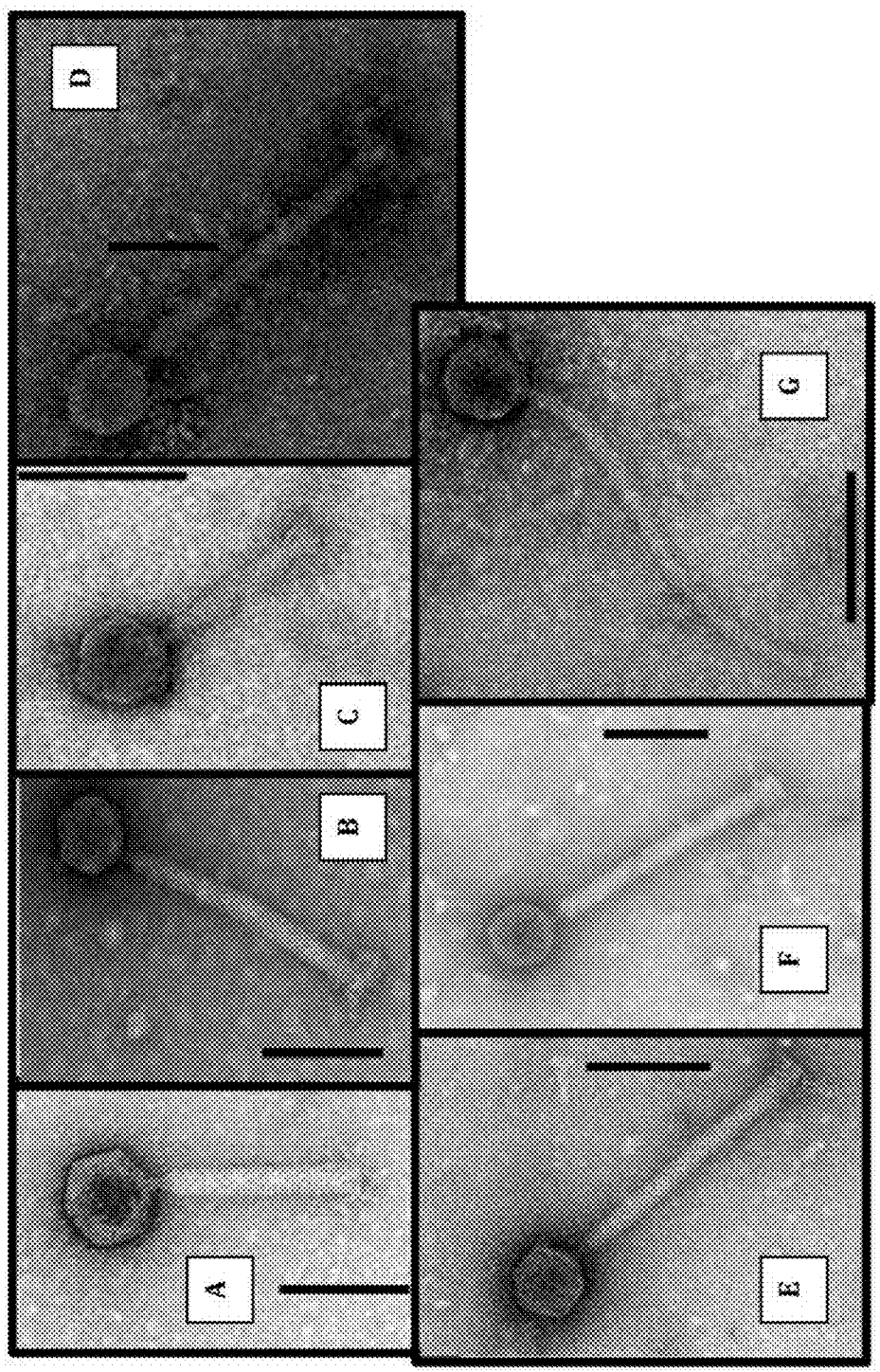

1. *C. difficile* Phage Purification and Isolation

Approximately 2 cm$^3$ of environmental soil samples from the UK, were enriched for the presence of bacteriophages using BHI (Brain Heart Infusion) media (Oxoid, U.K), and supplemented with 0.1% Sodium Taurocholate. The mixture was incubated for 10 days at 37° C. under anaerobic conditions. The enrichment cultures were centrifuged at 3398×g for 10 minutes and the supernatants filtered through 0.22 pore sized Millipore membranes.

Temperate phage isolation was performed following isolation of the environmental *C. difficile* strains on CCEY media (Bioconnections, U.K). The *C. difficile* were then induced for release of the prophage. To induce the prophage, either mitomycin C (3 μg/ml) or norfloxacin (6 μg/ml) was added to mid-log cultures (0.6 $OD_{550nm}$) of *C. difficile* isolates grown in BHI broth. The cultures were then incubated for 24 hours at 37° C. and under anaerobic conditions. Following incubation, the cultures were centrifuged at 3398×g for 10 minutes and the lysates filtered through 0.22 μm pore sized Millipore membranes. All phage samples were stored at 4° C. in the dark.

Phages were isolated by performing spot test assays of the phage samples on *C. difficile* bacterial lawns using the soft agar overlay method. For this method, 250 μl of overnight *C. difficile* culture was mixed with 3 ml BHI 0.4% soft agar, supplemented with 0.4 M $MgCl_2$ and 0.01 $CaCl_2$. The plated mixture was then poured onto a BHI 1% Agar plate. This was allowed to dry and the phage samples spotted onto the soft layer in 10 μl aliquots. Assays were incubated for 24 hours at 37° C. under anaerobic conditions. Resulting plaques, or clearings, were picked into 500 μl BHI and incubated overnight at 4° C. Phage samples were taken from clearings or plaques, then centrifuged at 10,000 g for 5 minutes and the supernatant retained. From these phage samples, three further rounds of plaque purification was performed.

2. Characterisation of the Phage Panel

Following purification (see section 1 above), isolated phages were propagated to high titre stocks and used for Pulsed Field Electrophoresis (PFGE) and Transmission Electron Microscopy (TEM); in order to characterise the phages through genome size and particle morphology.

Pulsed Field Gel Electrophoresis (PFGE) was performed on the purified phage. 40 μl Molten 2% Seqplaque agarose in 0.5×TBE buffer was added to 40 μl of phage sample (>10$^8$ PFU/ml) per plug and set 30-120 minutes at 4° C. Individual plugs were then digested overnight in 1 ml lysis buffer (100 mM EDTA, 100 mM Tris.Cl pH 9.0, 1% SDS and 0.5 mg/ml proteinase K) at 55° C. Plugs were then three times washed in TE buffer (Tris:EDTA pH8.0). Plugs were then assembled into 0.5×TBE 1% agarose gel with ladder alongside an appropriate size marker and run at 6 volts/com for 17 hours at 14° C. (Ramped pulse times were: initial 5 seconds; final 13 seconds). Gels were stained with ethidium bromide (at a concentration of 10 μg/ml) and visualised under longwave U.V. light.

PGFGE analysis identified genome sizes for each of the 7 identified phages; the results of which are found in table 1.

TABLE 1

Genome sizes determined using PGFGE

| Phage | ~Size (kbp) (+/−10%) |
|---|---|
| CD-HM1 | 50 |
| CD-HM2 | 50 |
| CD-HM3 | 50 |
| CD-HM4 | 50 |
| CD-HM5 | 50 |
| CD-HM6 | 50 |
| CD-HS1 | 40 |

Initial review of preliminary data on whole genome sequencing has confirmed that the size of the genome for CD-HM1 is ~54 kbp in length.

The results of the morphological characterisation of the phages using TEM can be found in FIG. 1.

3. Host Range Determination 3.1 First Determination

In order to determine the host range for the seven phages, they were first produced (propagated) on the host *C. difficile* strain that they infected most efficiently and on which consistently high phage titres were produced. These hosts are referred to as 'propagating hosts' or 'manufacturing hosts'. The manufacturing hosts were all isolated by the applicant, from environmental (CD105HE1 and CD105HS1) and clinical (CD105LC1) sources respectively and have been deposited in the HPA as shown below. CD-HM1, CDH-M2, CDH-M3 CDH-M5 and CDH-M6 are all propagated on CD105HE1 (ribotype 076). CDH-M4 is propagated on CD105HS1 (ribotype 012) and CD-HS1 is propagated on CD105LC1 (ribotype 027). All other studies discussed below followed the same manufacturing host relationship to phage.

CD105HE1 was deposited under HPA No 12081401
CD105LC1 was deposited under HPA No 12081402
CD105HS1 was deposited under HPA No. 12081403

A panel of *C. difficile* strains were used to determine the host range of the isolated phages. *C. difficile* strains were obtained both from environmental sources (UK) and clinical samples in the UK. The clinical samples were gratefully received from Leicester Hospital Trusts. All strains were PCR ribotyped and assigned their groups, according to the universal naming system, in the following manner.

*C. difficile* genomic DNA was extracted by re suspending a single colony taken from overnight cultures grown on BHI agar plate supplemented with 7% defibrinated Horse Blood in 150 μl of UPH$_2$O and 5% chelex resin (Biorad, U.K). Samples were heated to 100° C. for 12 minutes, cooled for 5 minutes and then centrifuged at 16,000 g for 10 minutes. Supernatants were then stored at 4° C. for future use.

PCR ribotyping was performed following DNA extraction from each strain using the Chelex protocol and using primers from Bidet et al (2000). For capillary gel electrophoresis, 12 μl of HotStarTaq Mix (Qiagen, U.K.) was added to 9 μl ultra-pure H$_2$O, 1 μl each primer and 1 μl Chelex DNA template. The forward primer used was fluorescently labelled with FAM (Invitrogen, U.K). The PCR product was then analysed by capillary gel electrophoresis, using 1 μl of template DNA with 9 μl of a master mix containing 9 μl Formaldehyde and 1 μl GeneScan™ 1200 LIZ® DNA ladder. Data analysis was performed on PeakScanner v1.0 (AppliedBiosystems) and ribotypes determined by comparing them to a known panel of ribotypes. Clarification was sought from Prof Mark Wilcox and Dr Warren Fawley (Leeds) who run the *Clostridium difficile* ribotyping network service.

Host range analysis was performed through the spot test assay described previously in section 1, but this time on *C. difficile* strains whose ribotypes were determined as above.

The results of the above host range determination analysis can be found in table 2.

TABLE 2

| Ribotype | | CD-HM 1 | CD-HM 2 | CD-HM 3 | CD-HM 4 | CD-HSI | CD-HM 5 | CD-HM 6 |
|---|---|---|---|---|---|---|---|---|
| 010 | H1b | 1 | 0 | 0 | 0 | 2 | 0 | 0 |
| | H3 | 0 | 0 | 0 | 0 | 2 | 0 | 0 |
| | H5d | 0 | 0 | 0 | 0 | 2 | 0 | 0 |
| | K16 | 0 | 0 | 0 | 0 | 2 | 0 | 0 |
| | R | 0 | 0 | 0 | 0 | 2 | 0 | 0 |
| | I | 0 | 2 | 0 | 0 | 0 | 2 | 2 |
| | R10 | 0 | 0 | 0 | 0 | 1 | 0 | 0 |
| 002 | AHE | 0 | 0 | 1 | 0 | 2 | 0 | 0 |
| | AIL | 0 | 0 | 1 | 0 | 0 | 0 | 0 |
| | AIJ | 0 | 0 | 1 | 0 | 0 | 0 | 0 |
| | ATH | 0 | 0 | 2 | 0 | 0 | 0 | 0 |
| | ATG | 0 | 0 | 1 | 0 | 2 | 0 | 0 |
| | AMP | 0 | 0 | 1 | 0 | 0 | 0 | 0 |
| | AQB | 0 | 0 | 1 | 0 | 0 | 0 | 0 |

TABLE 2-continued

Host range determination

| Ribotype | | CD-HM 1 | CD-HM 2 | CD-HM 3 | CD-HM 4 | CD-HSI | CD-HM 5 | CD-HM 6 |
|---|---|---|---|---|---|---|---|---|
| | ATB | 0 | 0 | 1 | 0 | 0 | 0 | 0 |
| | H15 | 1 | 0 | 0 | 0 | 2 | 0 | 2 |
| | K14 | 1 | 0 | 0 | 0 | 0 | 0 | 0 |
| | O | 0 | 0 | 0 | 0 | 1 | 0 | 0 |
| | P | 1 | 0 | 0 | 0 | 1 | 0 | 0 |
| | S | 0 | 0 | 0 | 0 | 1 | 0 | 0 |
| 003 | BUB | 0 | 0 | 0 | 0 | 0 | 0 | 0 |
| | BUL | 0 | 0 | 0 | 0 | 0 | 0 | 0 |
| 005 | H5b | 0 | 0 | 0 | 0 | 2 | 0 | 0 |
| | K18 | 0 | 0 | 0 | 0 | 2 | 0 | 0 |
| | E | 0 | 0 | 0 | 0 | 0 | 0 | 0 |
| | APA | 0 | 0 | 2 | 0 | 0 | 0 | 0 |
| | AIN | 0 | 0 | 1 | 0 | 0 | 0 | 0 |
| | AUE | 0 | 0 | 0 | 0 | 0 | 0 | 0 |
| | ASU | 0 | 0 | 1 | 0 | 2 | 0 | 0 |
| 009 | BRX | 0 | 0 | 0 | 0 | 0 | 0 | 0 |
| | BRQ | 0 | 0 | 0 | 0 | 0 | 0 | 0 |
| 010 | BSV | 0 | 0 | 0 | 0 | 0 | 0 | 0 |
| | BTQ | 0 | 0 | 0 | 0 | 2 | 0 | 0 |
| 013 | ARS | 0 | 0 | 0 | 0 | 0 | 0 | 0 |
| | ASH | 0 | 0 | 2 | 0 | 0 | 0 | 0 |
| | ASK | 2 | 0 | 1 | 0 | 2 | 0 | 0 |
| | AQZ | 1 | 0 | 2 | 0 | 0 | 0 | 0 |
| 014/ | AJZ | 2 | 2 | 1 | 0 | 2 | 2 | 2 |
| 020 | ANS | 2 | 2 | 1 | 0 | 0 | 2 | 0 |
| | AME | 1 | 2 | 1 | 0 | 0 | 2 | 2 |
| | AMR | 2 | 0 | 1 | 0 | 0 | 0 | 0 |
| | ARN | 2 | 0 | 0 | 0 | 0 | 0 | 0 |
| | AOE | 2 | 2 | 2 | 0 | 2 | 2 | 2 |
| | ATJ | 2 | 2 | 2 | 0 | 0 | 2 | 2 |
| | ATT | 2 | 2 | 2 | 0 | 0 | 2 | 2 |
| | AHR | 2 | 2 | 2 | 0 | 2 | 2 | 2 |
| | AOU | 2 | 2 | 2 | 0 | 2 | 2 | 2 |
| | ARW | 2 | 2 | 2 | 0 | 2 | 2 | 2 |
| | AQI | 2 | 1 | 1 | 0 | 0 | 2 | 0 |
| | AQM | 2 | 0 | 0 | 0 | 2 | 2 | 2 |
| | AQQ | 2 | 1 | 1 | 0 | 0 | 2 | 0 |
| | AST | 1 | 2 | 1 | 0 | 0 | 0 | 0 |
| | AIV | 2 | 1 | 1 | 0 | 0 | 2 | 2 |
| | OA | 1 | 2 | 0 | 0 | 1 | 2 | 2 |
| | K6 | 0 | 0 | 0 | 0 | 0 | 2 | 2 |
| | V | 2 | 2 | 0 | 0 | 2 | 0 | 0 |
| 017 | BTJ | 0 | 0 | 0 | 0 | 0 | 0 | 0 |
| 031 | BRN | 0 | 0 | 0 | 0 | 0 | 0 | 0 |
| 035 | BUM | 0 | 0 | 0 | 0 | 0 | 0 | 0 |
| 046 | K4 | 0 | 0 | 0 | 0 | 2 | 0 | 0 |
| 001 | H8 | 0 | 0 | 0 | 0 | 1 | 0 | 0 |
| | H4 | 0 | 0 | 0 | 0 | 2 | 0 | 0 |
| | H18 | 0 | 0 | 0 | 0 | 1 | 0 | 0 |
| | K? | 0 | 0 | 0 | 0 | 2 | 0 | 0 |
| | F | 0 | 0 | 0 | 0 | 2 | 0 | 0 |
| 015 | AHS | 0 | 0 | 0 | 0 | 0 | 0 | 0 |
| | ATU | 0 | 0 | 1 | 0 | 0 | 0 | 0 |
| | ATO | 0 | 0 | 0 | 0 | 0 | 2 | 0 |
| | ATM | 0 | 0 | 2 | 0 | 0 | 2 | 0 |
| | ANC | 0 | 1 | 1 | 0 | 0 | 0 | 0 |
| | APL | 0 | 0 | 0 | 0 | 0 | 0 | 0 |
| | ARD | 0 | 1 | 0 | 0 | 0 | 0 | 0 |
| | AHK | 0 | 0 | 0 | 0 | 2 | 0 | 0 |
| | ARB | 0 | 0 | 0 | 0 | 0 | 0 | 0 |
| | ATR | 0 | 0 | 0 | 0 | 0 | 0 | 0 |
| | ASO | 0 | 0 | 2 | 0 | 0 | 0 | 0 |
| | Q | 0 | 0 | 0 | 0 | 0 | 0 | 0 |
| 023 | AKL | 0 | 0 | 2 | 0 | 0 | 0 | 0 |
| 026 | AII | 0 | 0 | 0 | 0 | 2 | 2 | 2 |
| | AQA | 0 | 0 | 0 | 0 | 0 | 2 | 2 |
| | ARU | 2 | 0 | 0 | 0 | 2 | 0 | 0 |
| | C | 0 | 0 | 2 | 0 | 0 | 0 | 0 |
| | AIU | 0 | 0 | 2 | 0 | 2 | 0 | 0 |
| | 14L | 0 | 0 | 2 | 0 | 2 | 0 | 0 |
| | 2L | 0 | 0 | 2 | 0 | 2 | 0 | 0 |
| | 12L | 0 | 0 | 2 | 0 | 2 | 0 | 0 |
| | 83L | 0 | 0 | 2 | 0 | 2 | 0 | 0 |
| | 17L | 0 | 0 | 2 | 0 | 2 | 0 | 0 |
| | 67L | 0 | 0 | 2 | 0 | 2 | 0 | 0 |
| | 5L | 0 | 0 | 2 | 0 | 2 | 0 | 0 |

TABLE 2-continued

Host range determination

| Ribotype | | CD-HM 1 | CD-HM 2 | CD-HM 3 | CD-HM 4 | CD-HSI | CD-HM 5 | CD-HM 6 |
|---|---|---|---|---|---|---|---|---|
| | 26L | 0 | 0 | 2 | 0 | 2 | 0 | 0 |
| | 94L | 0 | 0 | 2 | 0 | 2 | 0 | 0 |
| | 90L | 0 | 0 | 2 | 0 | 2 | 0 | 0 |
| | 63L | 0 | 0 | 2 | 0 | 2 | 0 | 0 |
| | 22L | 0 | 0 | 2 | 0 | 2 | 0 | 0 |
| | 23L | 0 | 0 | 2 | 0 | 2 | 0 | 0 |
| | 31L | 0 | 0 | 2 | 0 | 2 | 0 | 0 |
| | 3L | 0 | 0 | 2 | 0 | 2 | 0 | 0 |
| | 49L | 0 | 0 | 2 | 0 | 2 | 0 | 0 |
| | 37L | 0 | 0 | 2 | 0 | 2 | 0 | 0 |
| | 13L | 0 | 0 | 2 | 0 | 2 | 0 | 0 |
| | 53L | 0 | 0 | 2 | 0 | 2 | 0 | 0 |
| | 40L | 0 | 0 | 2 | 0 | 2 | 0 | 0 |
| | 36L | 0 | 0 | 2 | 0 | 2 | 0 | 0 |
| | 72L | 0 | 0 | 2 | 0 | 2 | 0 | 0 |
| | K15 | 0 | 0 | 0 | 0 | 2 | 2 | 0 |
| 027 | HB | 0 | 0 | 0 | 0 | 2 | 0 | 0 |
| 050 | BRU | 0 | 0 | 0 | 0 | 2 | 0 | 0 |
| 078 | AKD | 0 | 0 | 0 | 0 | 0 | 0 | 0 |
| | ALL | 0 | 0 | 2 | 0 | 0 | 0 | 0 |
| | AKX | 0 | 0 | 0 | 0 | 0 | 0 | 0 |
| | ANL | 0 | 0 | 2 | 0 | 0 | 0 | 0 |
| | AMC | 0 | 0 | 0 | 0 | 0 | 0 | 0 |
| | AIA | 0 | 0 | 0 | 0 | 0 | 0 | 0 |
| | AMT | 0 | 0 | 0 | 0 | 0 | 0 | 0 |
| | ASS | 0 | 0 | 0 | 0 | 0 | 0 | 0 |
| | AUG | 0 | 0 | 0 | 0 | 0 | 0 | 0 |
| | AIK | 0 | 0 | 0 | 0 | 0 | 0 | 0 |
| | AIG | 0 | 0 | 0 | 0 | 0 | 0 | 0 |
| | ANP | 0 | 0 | 0 | 0 | 0 | 0 | 0 |
| | ALE | 0 | 0 | 0 | 0 | 0 | 0 | 0 |
| | AML | 0 | 0 | 0 | 0 | 0 | 0 | 0 |
| | H17 | 0 | 0 | 0 | 0 | 0 | 0 | 0 |
| | H5c | 0 | 0 | 0 | 0 | 0 | 0 | 0 |
| | J | 0 | 0 | 0 | 0 | 0 | 0 | 0 |
| 081 | ANO | 0 | 0 | 0 | 0 | 0 | 0 | 0 |
| 087 | AIH | 2 | 0 | 2 | 0 | 0 | 2 | 2 |
| | APT | 0 | 0 | 1 | 0 | 0 | 0 | 0 |
| | ATX | 0 | 0 | 1 | 0 | 2 | 0 | 0 |
| 106 | BTW | 0 | 0 | 0 | 0 | 2 | 0 | 0 |
| | BUP | 0 | 0 | 0 | 0 | 2 | 0 | 0 |
| | BUN | 0 | 0 | 0 | 0 | 2 | 0 | 0 |
| 107 | AQR | 0 | 0 | 0 | 0 | 2 | 0 | 0 |
| | ASQ | 0 | 0 | 0 | 0 | 0 | 0 | 0 |
| | ASE | 0 | 0 | 0 | 0 | 0 | 0 | 0 |
| | ARJ | 0 | 0 | 0 | 0 | 0 | 0 | 0 |
| | ARZ | 0 | 0 | 0 | 0 | 0 | 0 | 0 |
| | ARD | 0 | 0 | 0 | 0 | 2 | 0 | 0 |
| | ASX | 0 | 0 | 0 | 0 | 0 | 0 | 0 |
| | AUC | 0 | 0 | 0 | 0 | 0 | 0 | 0 |
| | AUD | 0 | 0 | 0 | 0 | 2 | 0 | 0 |
| | AUI | 0 | 0 | 0 | 0 | 0 | 0 | 0 |
| 012 | K10 | 0 | 2 | 0 | 2 | 0 | 0 | 0 |
| 031 | H11 | 0 | 0 | 2 | 2 | 0 | 0 | 0 |
| | H1a | 0 | 0 | 2 | 0 | 0 | 0 | 0 |
| | M | 0 | 0 | 0 | 2 | 1 | 0 | 0 |
| 106 | H19 | 0 | 0 | 0 | 0 | 2 | 0 | 0 |
| 220 | H12 | 0 | 0 | 0 | 0 | 0 | 1 | 1 |
| | K3 | 0 | 2 | 0 | 0 | 0 | 1 | 1 |
| | K12 | 0 | 0 | 0 | 0 | 0 | 2 | 2 |
| | N | 0 | 0 | 0 | 0 | 1 | 0 | 0 |
| | K | 2 | 2 | 2 | 0 | 0 | 0 | 0 |
| | Y | 2 | 2 | 2 | 0 | 0 | 2 | 2 |
| | U | 0 | 0 | 0 | 0 | 0 | 0 | 0 |
| | L | 0 | 0 | 0 | 0 | 2 | 0 | 0 |
| 076 | T6 | 2 | 2 | 2 | 0 | 0 | 2 | 2 |
| 085 | R8 | 0 | 0 | 0 | 0 | 0 | 0 | 0 |
| 021 | B2 | 0 | 0 | 0 | 0 | 0 | 0 | 0 |
| | B1 | 0 | 0 | 0 | 0 | 0 | 0 | 0 |
| | K9 | 0 | 0 | 0 | 0 | 0 | 0 | 0 |
| | A | 0 | 0 | 0 | 0 | 0 | 0 | 0 |
| 003 | SS1 | 0 | 0 | 0 | 0 | 0 | 0 | 0 |
| 137 | G | 0 | 0 | 0 | 0 | 0 | 0 | 0 |
| | D | 0 | 0 | 0 | 0 | 0 | 0 | 0 |

In most cases, the analysis of host specificity for each ribotype was tested using a number of colonies of *C. diff* from different origins that had all been identified as being of the same ribotype. The second column in table 2 indicates each of the separate colonies used during analysis of each ribotype (each letter-numerical code represents a different colony from a different origin). A value of 2 in table 2 represents a clearing on the *C. difficile* lawn following a spot test, and so demonstrates the ability of the tested phage to kill *C. difficile* of that specified ribotype. A value of 1 in table 2 signifies that turbid plaques were identified on the *C. difficile* lawn following a spot test, which indicates that the phage that was tested was able to kill *C. difficile* of that specified ribotype. Finally, a value of 0 in table 2 signifies that there was no clearing or turbid plaques on the *C. difficile* lawn following a spot test, which indicates that the phage tested was not capable of killing, or was of insufficient titre to kill, *C. difficile* of that specified ribotype.

3.2 Second Determination

Following the study discussed above in paragraph 3.1, a similar study was carried out using *C. difficile* derived from three geographical origins; clinical samples from the UK, from the US and from Australia. All strains were PCR ribotyped and assigned their group, according to the universal naming system, in the manner discussed above in paragraph 3.1. Generally higher titres of phage were used in the second determination when compared to the first determination.

Host range analysis has been performed through the spot test assay described previously in section 1, but this time on the *C. difficile* strains of the second study.

The results of the above host range determination analysis can be found in table 4.

TABLE 4

Host Range Determination

| Ribotypes | Origin | Strains | Phages CD-HM1 | CD-HM2 | CD-HM3 | CD-HM4 | CD-HS1 | CD-HM5 | CD-HM6 |
|---|---|---|---|---|---|---|---|---|---|
| 001 | AU | AUS1025 | 0 | 0 | 0 | 0 | 2 | 0 | 0 |
|  | AU | AUS1021 | 0 | 0 | 0 | 0 | 2 | 0 | 0 |
|  | UK | AIP | 0 | 0 | 0 | 0 | 2 | 0 | 0 |
|  | UK | CD001 | 0 | 0 | 0 | 0 | 2 | 0 | 0 |
| 002 | UK | TL178 | 0 | 0 | 1 | 0 | 0 | 0 | 0 |
|  | UK | ATH | 0 | 1 | 1 | 0 | 0 | 0 | 1 |
|  | AU | AUS1036 | 2 | 2 | 2 | 0 | 0 | 1 | 0 |
|  | UK | AIL | 0 | 1 | 1 | 0 | 0 | 1 | 1 |
|  | UK | AIJ | 0 | 1 | 1 | 0 | 0 | 0 | 1 |
|  | AU | AUS1033 | 0 | 0 | 1 | 0 | 0 | 0 | 0 |
| 003 | UK | LEEDS003 | 2 | 2 | 0 | 0 | 0 | 0 | 0 |
|  | UK | AQV | 2 | 2 | 0 | 0 | 1 | 0 | 0 |
|  | US | 2007831 | 0 | 1 | 1 | 1 | 1 | 0 | 1 |
| 005 | UK | AUE | 0 | 0 | 0 | 0 | 0 | 0 | 0 |
| 012 | UK | CD630 | 0 | 0 | 0 | 0 | 0 | 0 | 0 |
| 013 | UK | ASA | 0 | 0 | 0 | 0 | 0 | 0 | 0 |
|  | UK | ARS | 0 | 2 | 2 | 0 | 1 | 2 | 2 |
| 014/020 | UK | ATJ | 2 | 2 | 2 | 0 | 0 | 2 | 2 |
|  | UK | ATT | 2 | 2 | 2 | 0 | 0 | 2 | 2 |
|  | UK | ATK | 2 | 2 | 2 | 0 | 0 | 2 | 2 |
|  | UK | TL176 | 2 | 2 | 2 | 0 | 0 | 2 | 2 |
|  | AU | AUS1022 | 0 | 0 | 2 | 0 | 0 | 0 | 2 |
|  | UK | AIP | 2 | 2 | 2 | 0 | 0 | 2 | 2 |
| 015 | UK | TL174 | 0 | 0 | 0 | 0 | 0 | 0 | 0 |
|  | UK | ALV | 0 | 0 | 0 | 0 | 2 | 0 | 0 |
|  | UK | ATO | 0 | 0 | 1 | 0 | 0 | 1 | 0 |
|  | UK | ATU | 0 | 0 | 0 | 0 | 0 | 0 | 1 |
|  | UK | ATR | 0 | 0 | 0 | 0 | 0 | 0 | 1 |
| 017 | AU | AUS1023 | 0 | 0 | 0 | 0 | 0 | 0 | 0 |
|  | UK | CFS | 0 | 0 | 0 | 0 | 0 | 0 | 0 |
|  | UK | M68 | 0 | 0 | 0 | 0 | 0 | 0 | 0 |
|  | UK | LEEDS017 | 0 | 0 | 0 | 0 | 0 | 0 | 0 |
| 018 | UK | LEEDS018 | 2 | 2 | 2 | 1 | 1 | 1 | 1 |
| 023 | UK | CD305 | 0 | 0 | 0 | 0 | 0 | 0 | 0 |
|  | UK | AKL | 1 | 0 | 1 | 0 | 0 | 1 | 1 |
|  | UK | AJX | 1 | 0 | 1 | 0 | 0 | 1 | 1 |
|  | UK | LEEDS023 | 0 | 0 | 1 | 0 | 1 | 0 | 0 |
| 026 | UK | ALN | 0 | 0 | 0 | 0 | 0 | 2 | 0 |
|  | AU | AUS1028 | 0 | 0 | 0 | 0 | 0 | 0 | 0 |
|  | UK | AUB | 0 | 0 | 0 | 0 | 0 | 0 | 0 |
| 027 | AU | AUS1032 | 0 | 0 | 0 | 0 | 2 | 0 | 0 |
|  | UK | CD196 | 0 | 0 | 0 | 0 | 2 | 0 | 0 |
|  | UK | R20291 | 0 | 0 | 0 | 0 | 2 | 0 | 0 |
|  | UK | B109 | 0 | 0 | 0 | 0 | 2 | 0 | 0 |
|  | UK | AJS | 0 | 0 | 0 | 0 | 2 | 0 | 0 |
|  | AU | AUS1024 | 0 | 0 | 0 | 0 | 2 | 0 | 0 |
|  | UK | AJV | 0 | 0 | 1 | 0 | 2 | 0 | 0 |
|  | US | US027 | 0 | 0 | 0 | 0 | 2 | 0 | 0 |
|  | US | 2006237 | 0 | 0 | 0 | 0 | 2 | 0 | 0 |
| 078 | UK | AIG | 0 | 0 | 0 | 0 | 0 | 0 | 0 |
|  | UK | AIK | 0 | 0 | 0 | 0 | 0 | 0 | 0 |
|  | UK | M120 | 0 | 0 | 0 | 0 | 0 | 0 | 0 |

TABLE 4-continued

Host Range Determination

| Ribotypes | Origin | Strains | Phages CD-HM1 | CD-HM2 | CD-HM3 | CD-HM4 | CD-HS1 | CD-HM5 | CD-HM6 |
|---|---|---|---|---|---|---|---|---|---|
| | UK | ATM | 0 | 0 | 0 | 0 | 0 | 0 | 0 |
| | US | 5361 | 0 | 0 | 0 | 0 | 0 | 0 | 0 |
| 081 | UK | ANO | 0 | 0 | 0 | 0 | 2 | 0 | 0 |
| | UK | ANQ | 0 | 0 | 0 | 0 | 2 | 0 | 0 |
| 087 | UK | APX | 0 | 0 | 1 | 0 | 0 | 0 | 0 |
| | UK | APT | 0 | 0 | 0 | 1 | 1 | 0 | 0 |
| 106 | UK | CD106 | 2 | 2 | 1 | 0 | 0 | 0 | 0 |
| | UK | LV22 | 2 | 2 | 2 | 0 | 0 | 2 | 0 |
| 107 | UK | ASV | 0 | 0 | 0 | 0 | 0 | 0 | 0 |
| | UK | ASQ | 0 | 0 | 0 | 0 | 2 | 0 | 0 |
| 126 | US | 2005093 | 0 | 0 | 0 | 0 | 0 | 0 | 0 |
| 262 | US | 2007827 | 0 | 0 | 0 | 0 | 0 | 0 | 0 |
| Total = 20 | | | 64 | 13 | 16 | 24 | 4 | 22 | 14 | 16 |

The phage-killing/lysis efficacy values provided in table 4 are given values of 0, 1 or 2. These values correspond to the same efficacy designations provided in table 2 above.

4. Deposit of Phages

All 7 phages have been deposited with the National Collection of Type Cultures (NCTC) on 14 Aug. 2012. Each of the phages has been given the depository number shown in table 3.

TABLE 3

NCTC deposit number

| Phage | Accession No. |
|---|---|
| CD-HM1 | NCTC 12081410 |
| CD-HM2 | NCTC 12081409 |
| CD-HM3 | NCTC 12081408 |
| CD-HM4 | NCTC 12081407 |
| CD-HM5 | NCTC 12081406 |
| CD-HM6 | NCTC 12081405 |
| CD-HS1 | NCTC 12081404 |

5. In Vivo Analysis of Phage Virulence (Group 1)

Five Hamsters were used in this study (C1, C2, T1, T2, T3). C1 and C2 were used as controls and were not treated with phage CD-HM1 (also called phage 12), but were inoculated with $1.15 \times 10^4$ C. difficile spores ribotype 005 (1342) (also referred to as C. difficile 1342). T1-T3 were infected with $1.15 \times 10^4$ C. difficile ribotype 005 and treated with 3 doses of phage CD-HM1 every 8 hrs for 24 hours ($10^8$ pfu dose). Bacteriophage treated animals were given 400 µl of 1M sodium bicarbonate orally 30 min before administration of phage and C. difficile to neutralise the pH in the stomach.

All animals were culled at 24 hr post-infection and the numbers of bacteria and bacteriophage were enumerated.

Abbreviations:
Cae=Caecum
Col=Colon
TA=Tissue associated
LA=Lumen associated

After the animals were culled, the caecum and colon were removed. The organs were opened longitudinally and washed. Samples of the lumen associated gut wash (LA) were plated onto Braziers CCEY agar. The organs were then placed in stomacher bags in 5 ml of storage medium and stomached for 2 min to enumerate the number of bacteria associated with the tissue (TA), again by plating onto Braziers CCEY agar. Plates were incubated in the anaerobic cabinet for 48 hr.

Figure 2:
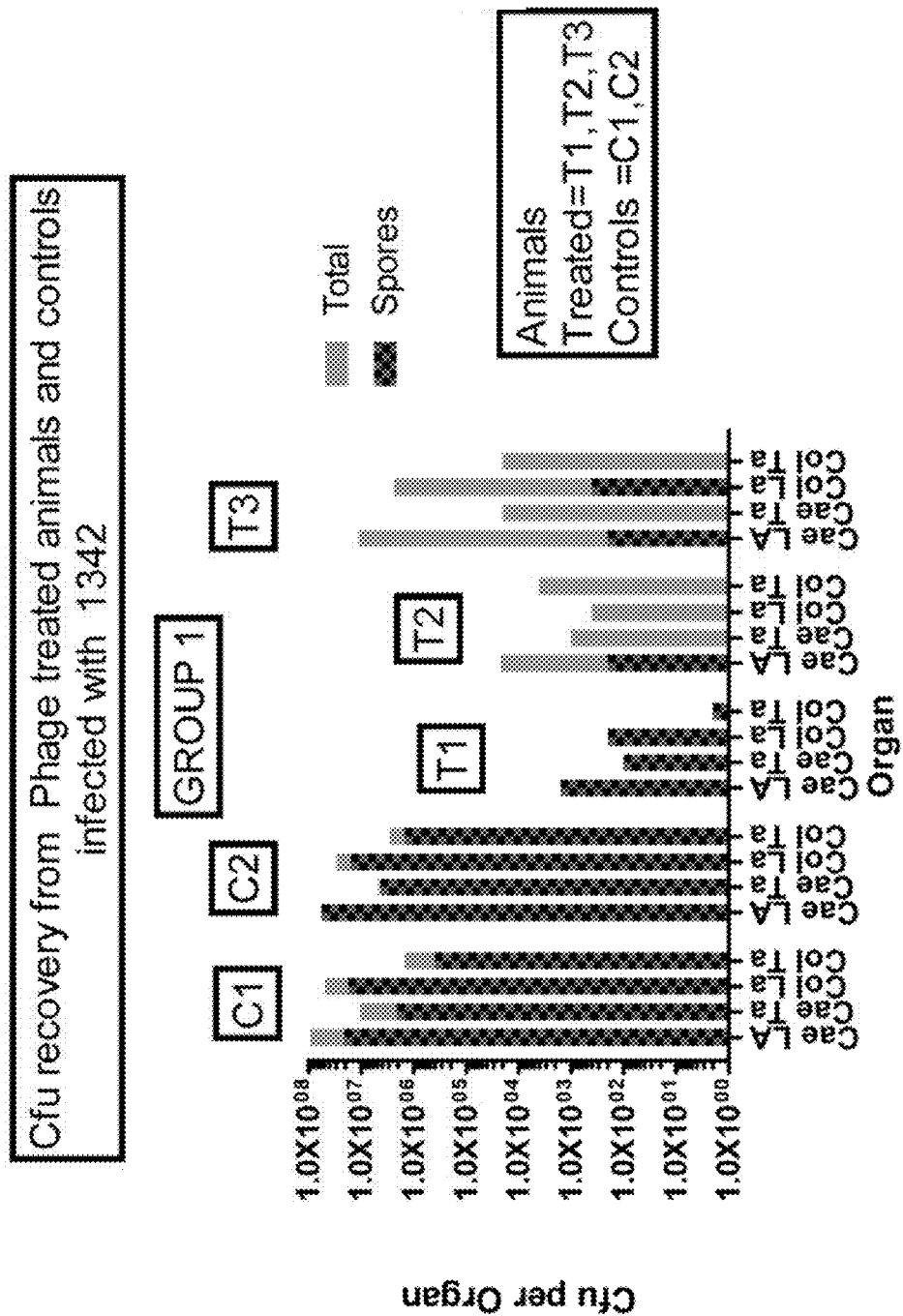

Results of this analysis can be found in FIG. 2.

Figure 3A:
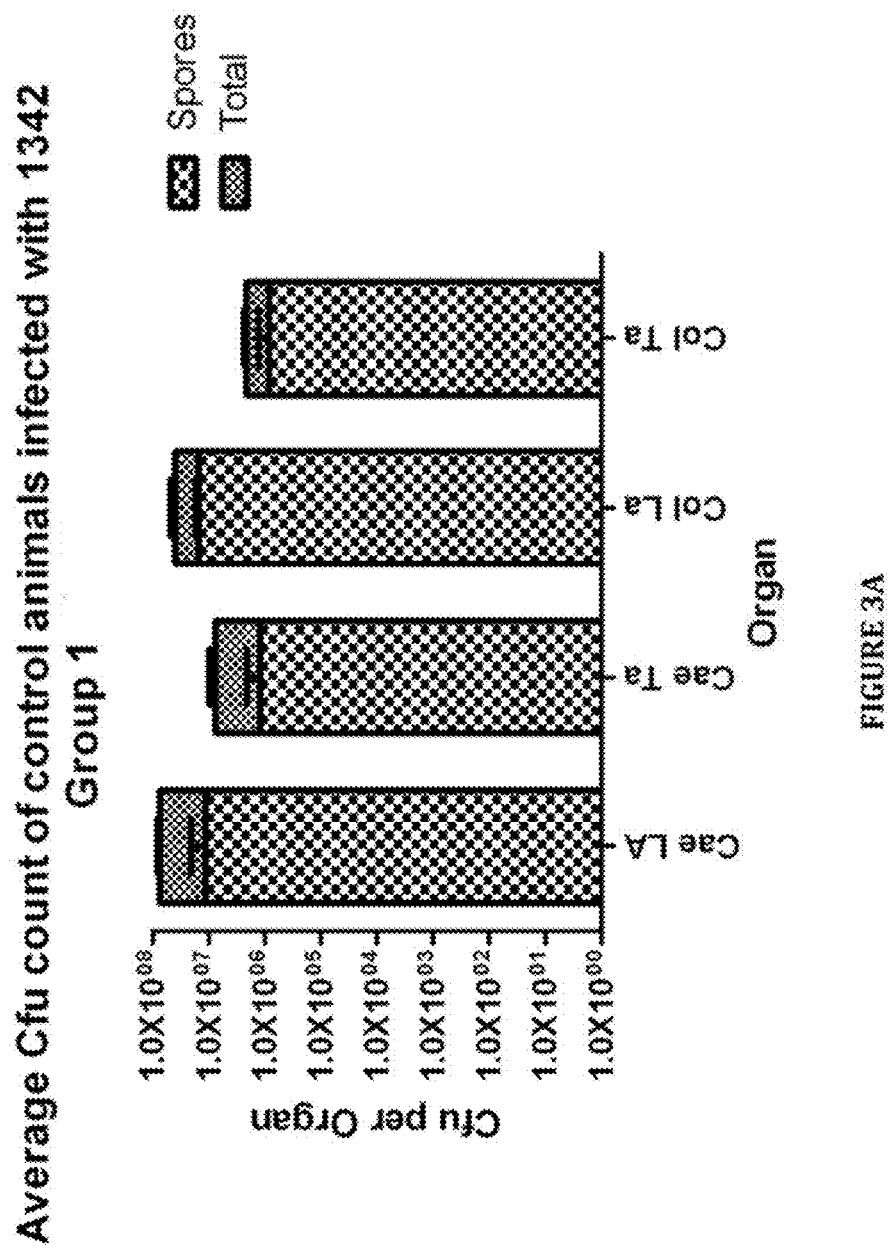
FIG. 3 shows the averaged values for the results provided in FIG. 2.
Figure 3B:
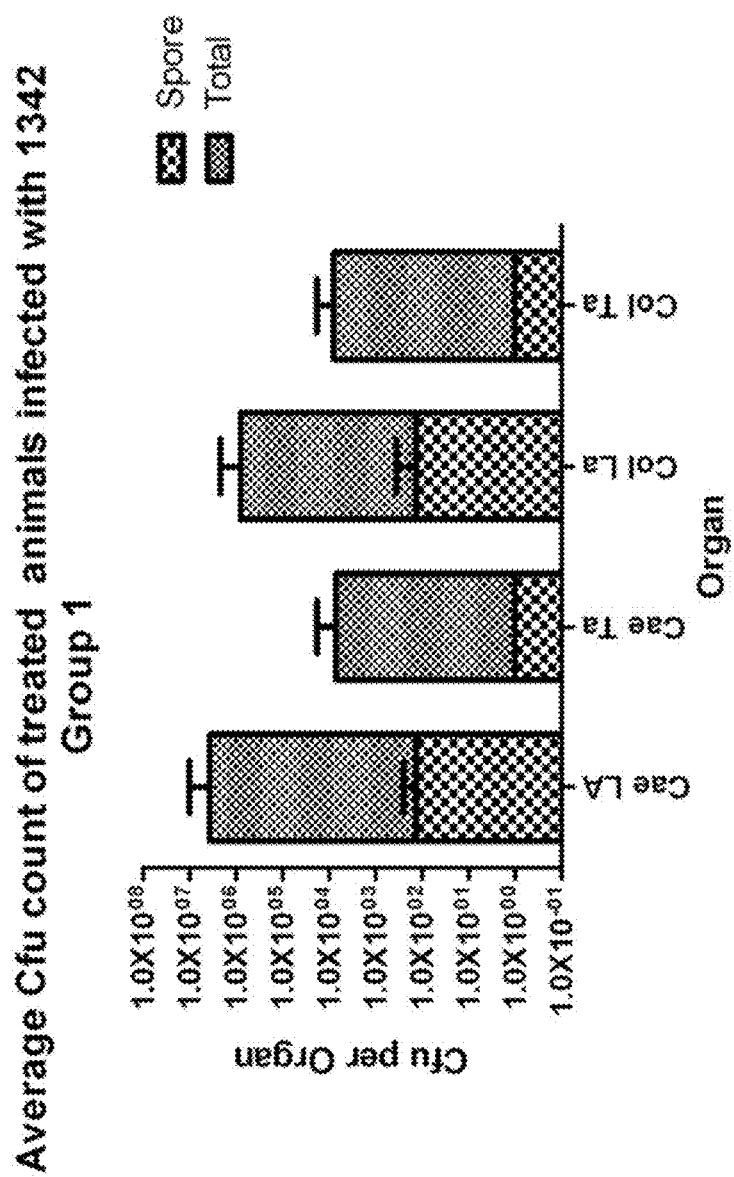

FIG. 3 shows pooled data for the animals receiving no phage (FIG. 3A) and those being treated with phage (FIG. 3b) from the study above. It is clear that there is a marked reduction in the colonisation with C. difficile ribotype 005 when animals are treated with bacteriophage.

The number of bacteriophage recovered from the lumen associated gut wash is carried out as follows:—

The numbers of bacteriophage were determined by dropping 10 µl of each filtered gut sample in triplicate onto a top agar containing C. difficile ribotype 076. Plates were incubated in the anaerobic cabinet for 24 hr and numbers of plaques were counted and the average PFU/ml was calculated.

Figure 4:
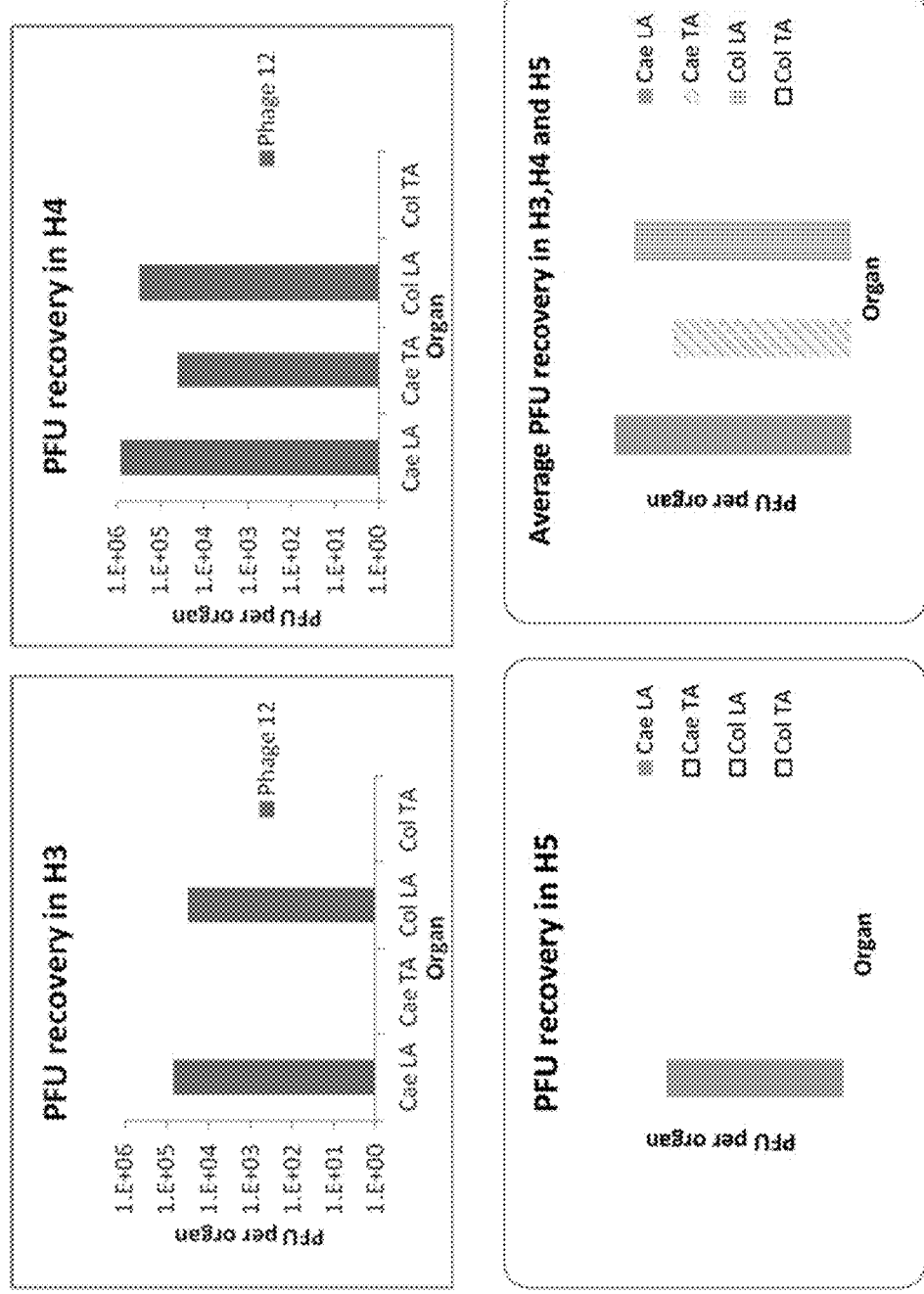
FIG. 4 shows number of bacteriophage recovered from T1-T3 (H3 to H5) following phage treatment.

FIG. 4 shows numbers of bacteriophage recovered from the gut of each of T1-T3 (i.e. H3-H5) from the above study. FIG. 4, bottom right, shows an average of the results for all the animals treated with phage. Phage 12 corresponds to CD-HM1.

Figure 5:
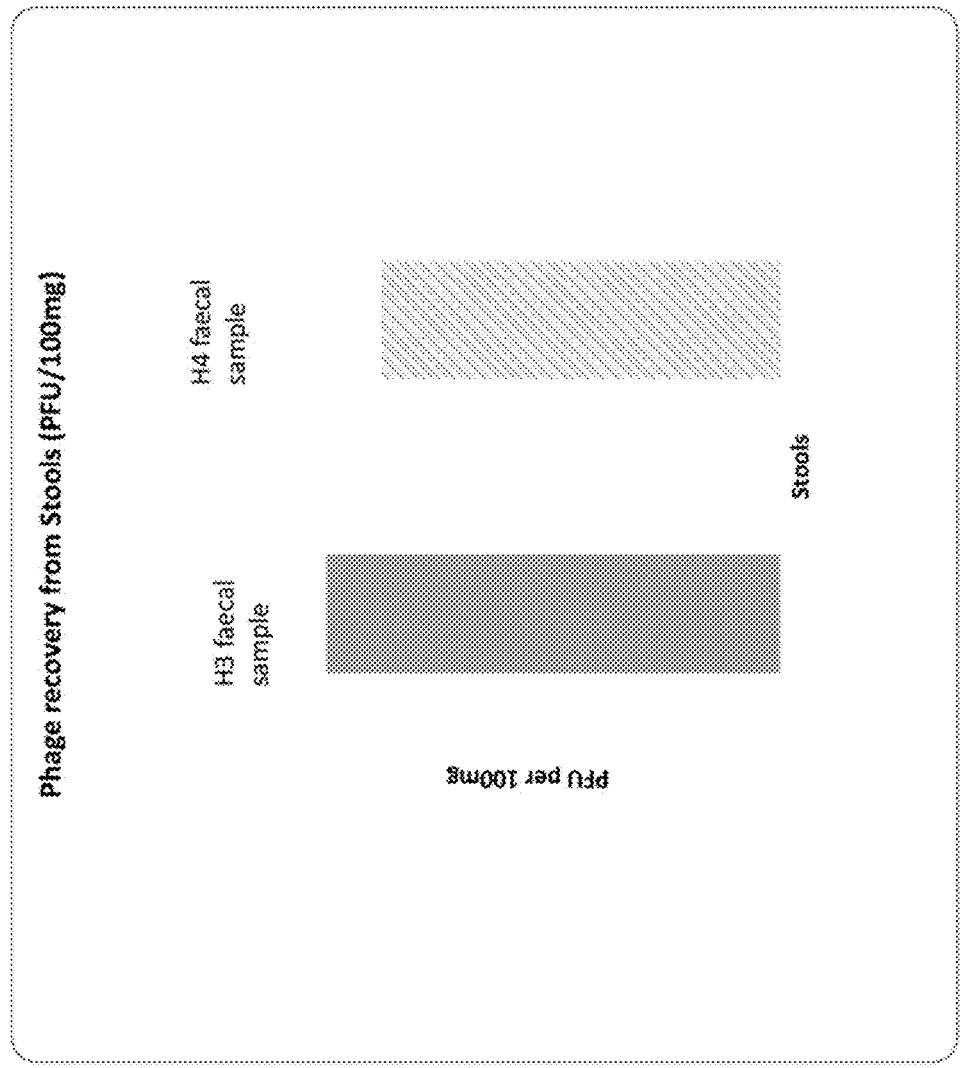
FIG. 5 shows the number of phage recovered from the stools of T1 and T2 (H3 and H4) following phage treatment.

FIG. 5 shows phage recovery from the stools (faeces) of animals T1 and T2 (i.e. H3 and H4) in the above study.

The results show that bacteriophage were isolated in high numbers in the lumen associated material in both the caecum and colon in 2 animals and was also found in faeces. This proves that bacteriophage can survive passage through the stomach and gut. T3 (H5) showed a higher bacterial count and also a lower titre of bacteriophage but the bacterial numbers were still much lower than non-treated animals.

The killing effect of bacteriophage also removed enough of the C. difficile-derived active toxin to avoid any adverse effect on the hamster gut. There were no clinical signs of infection observed i.e. no diarrhoea, lethargy or painful movement.

6. In Vivo Analysis Following Clindamycin Administration (Group 2)

Hamsters (C1, C2, T1, T2, T3) received an oral dose of clindamycin 30 mg/kg to disrupt their microbiota to enable C. difficile to colonise. Some animals received 400 µl of 1M sodium bicarbonate 30 min before administration of bacteria and bacteriophage. All were inoculated with $9.4 \times 10^3$ spores of C. difficile 005. T1-T3 additionally received CD-HM1 bacteriophage treatment. Bacteriophage were administered orally with three doses of 500 µl containing $1 \times 10^8$ pfu. at 8 hr intervals. All animals were culled at 24 hr post challenge.

Figure 6:
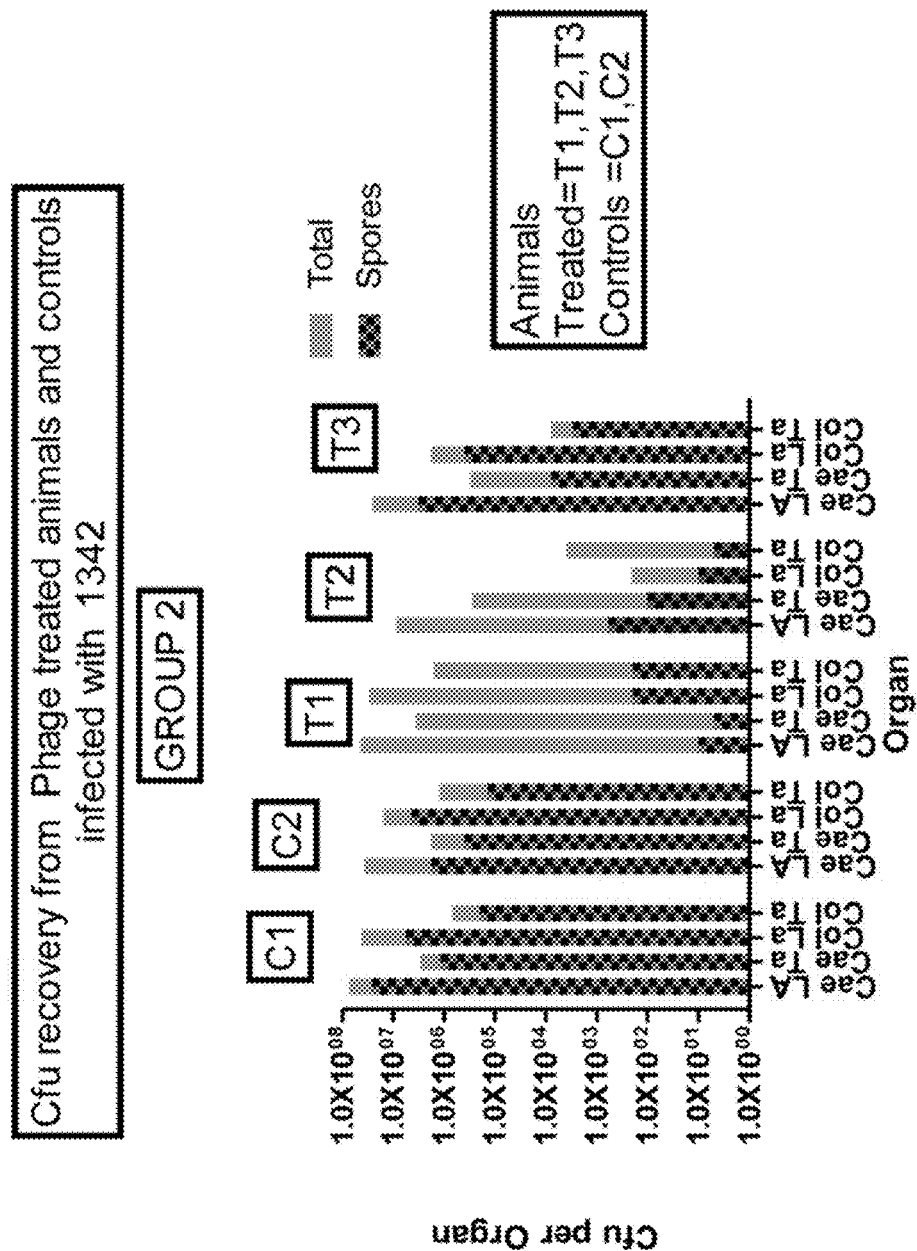
FIG. 6 shows the results of an analysis of the number of *C. diff* obtained from lumen associated gut wash and tissue of 5 hamsters (C1, C2, T1, T2, T3). All hamsters having been pre-treated with clindamycin.
Figure 7A:
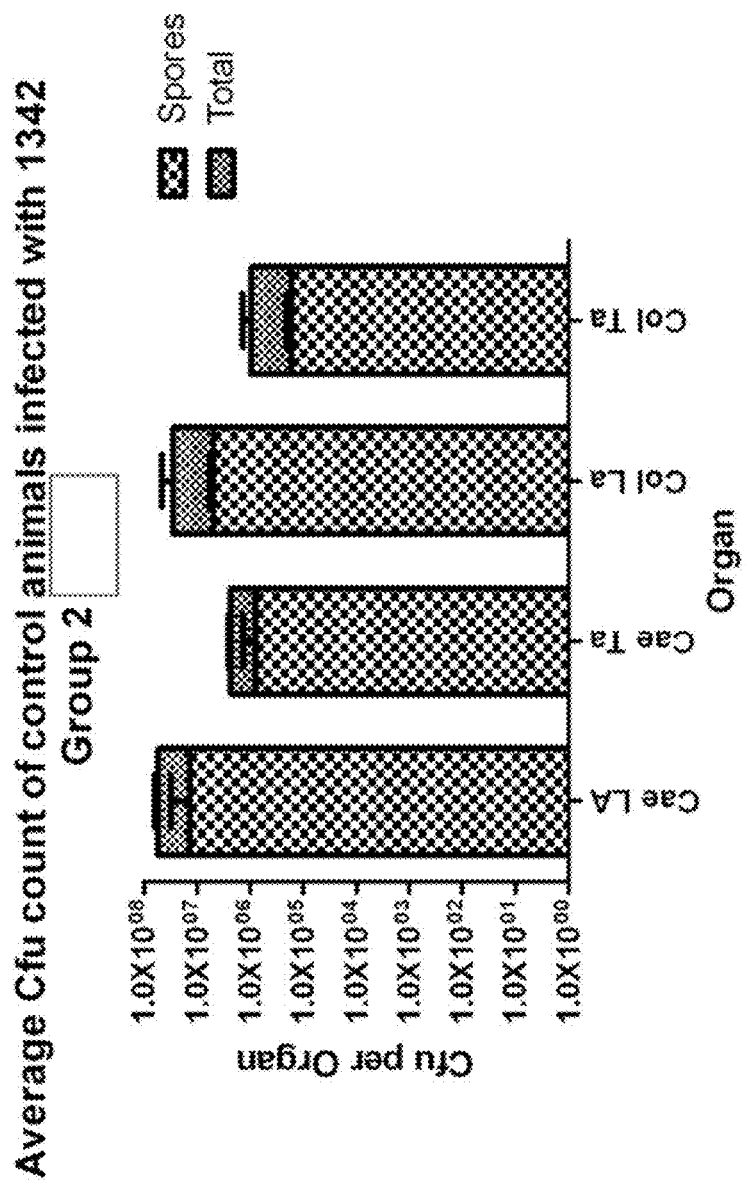
FIG. 7 shows the average results of those shown in FIG. 6.
Figure 7B:
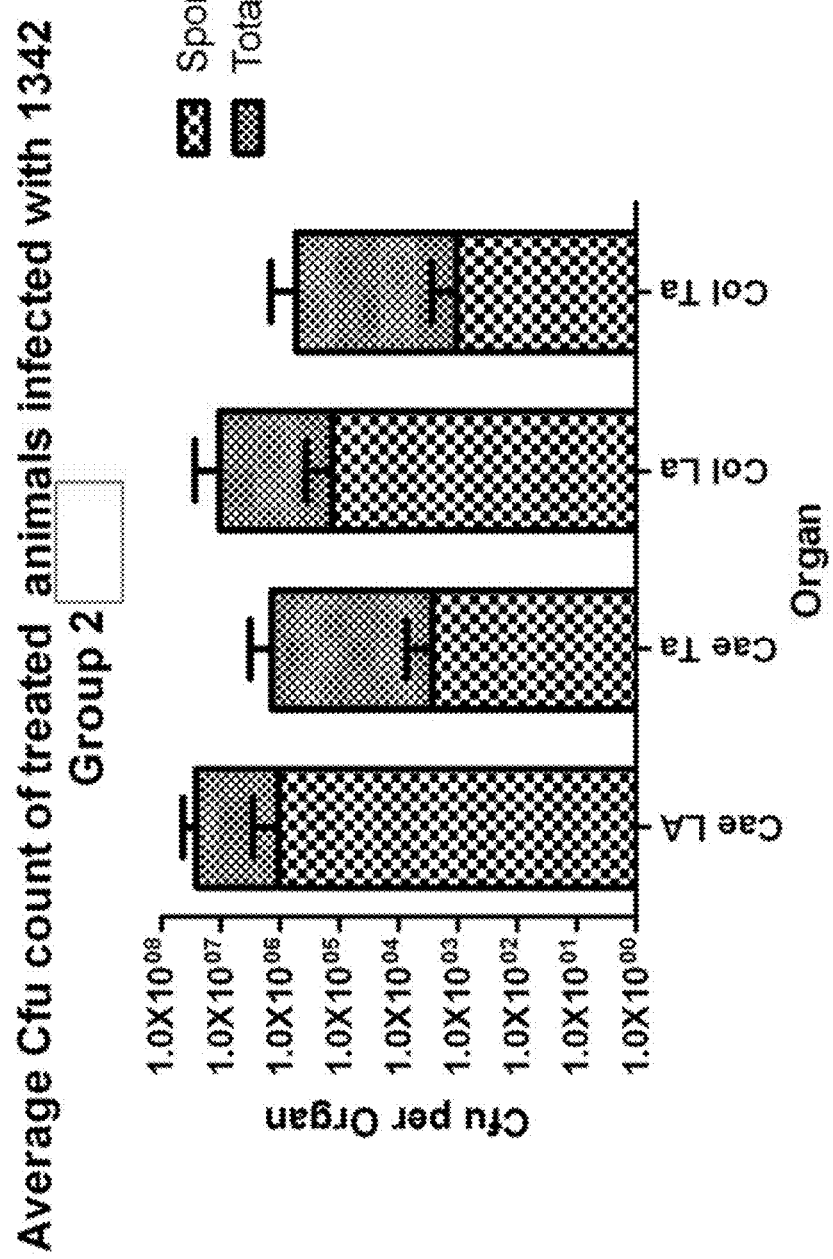

After the animals were culled the caecum and colon were removed. The organs were opened longitudinally and washed. Samples of the lumen associated gut wash (LA) were plated onto Braziers CCEY agar. Each organ was then placed in a stomacher bag in 5 ml of storage medium and stomached for 2 min allow the enumeration of the number of bacteria associated with the tissue (TA) by plating onto Braziers CCEY agar. Plates were incubated in an anaerobic cabinet for 48 hr. FIG. 6 provides the results of the calculation of the number of bacteria in the study. FIG. 7 shows the average of these results separated into control group (7A) and treated group (7B).

Bacteriophage phage recovery from the lumen associated gut wash is analysed as follows:—

Figure 8:
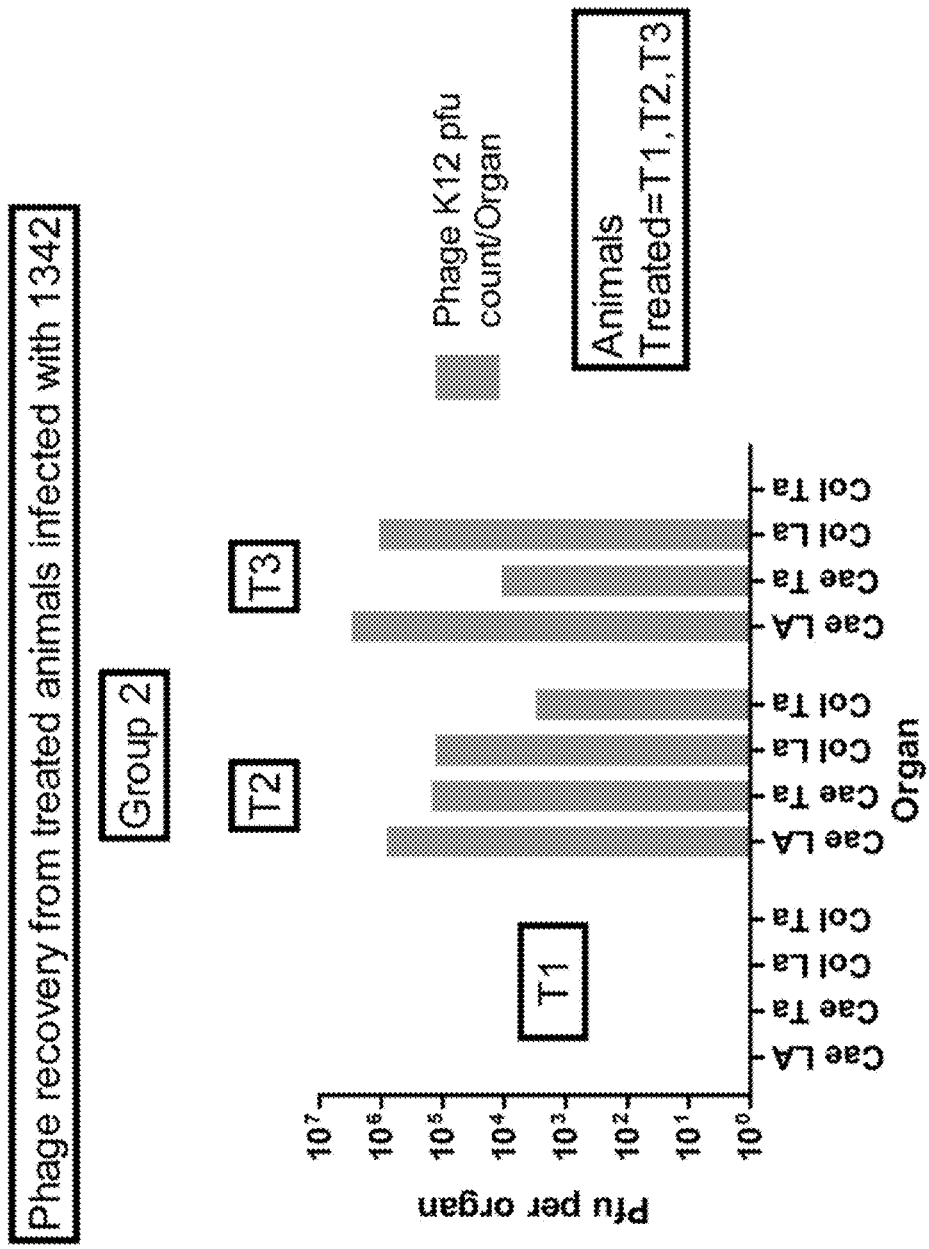
FIG. 8 shows the corresponding number of phages recovered from the different organs of the hamsters T1 to T3 (H3 to H5) following phage treatment.

The numbers of bacteriophage were determined by dropping 10 μl of each filtered gut sample in triplicate onto a top agar containing *C. difficile* ribotype 076. Plates were incubated in the anaerobic cabinet for 24 hr and numbers of plaques were counted and the average PFU/organ was calculated (PFU=plaque forming unit). The results of the analysis are shown in FIG. 8.

T1 and T2 received 1M sodium bicarbonate before challenge with *C. difficile* spores, ribotype 005 (1342). There was no significant difference in the colonisation of these animals at 24 hr compared with animals which were challenged without the neutralisation step (ie T3). This shows that sodium bicarbonate has no adverse effect on the infection profile of *C. difficile* ribotype 005 (1342) in the hamster model.

The results obtained were consistent with those discussed in section 6. There was a marked reduction in the colonisation with *C. difficile* ribotype 005 when animals are treated with bacteriophage.

Bacteriophage were isolated in high numbers from the lumen associated material in both the caecum and colon in two animals (T2 and T3) and were also found in faeces. This proves that bacteriophage can survive passage through the stomach and gut. T3 showed a higher bacterial count with no recovery of bacteriophages.

The bacterial numbers are much lower than control animals, especially the number of spores present.

There are little or no *C. difficile* spores present in the faecal material and bacteriophages are also present in this material.

Treatment with bacteriophages did not release toxins to the level where they had an impact on the hamster gut. There was no clinical signs of infection observed i.e. no diarrhoea, lethargy or painful movement. Samples of the colon and caecum were removed and prepared for histological examination to ensure that there was no visible damage to the gut due to the administration of bacteriophage.

7. Impact of Phage on Disease Prevention

Figure 9:
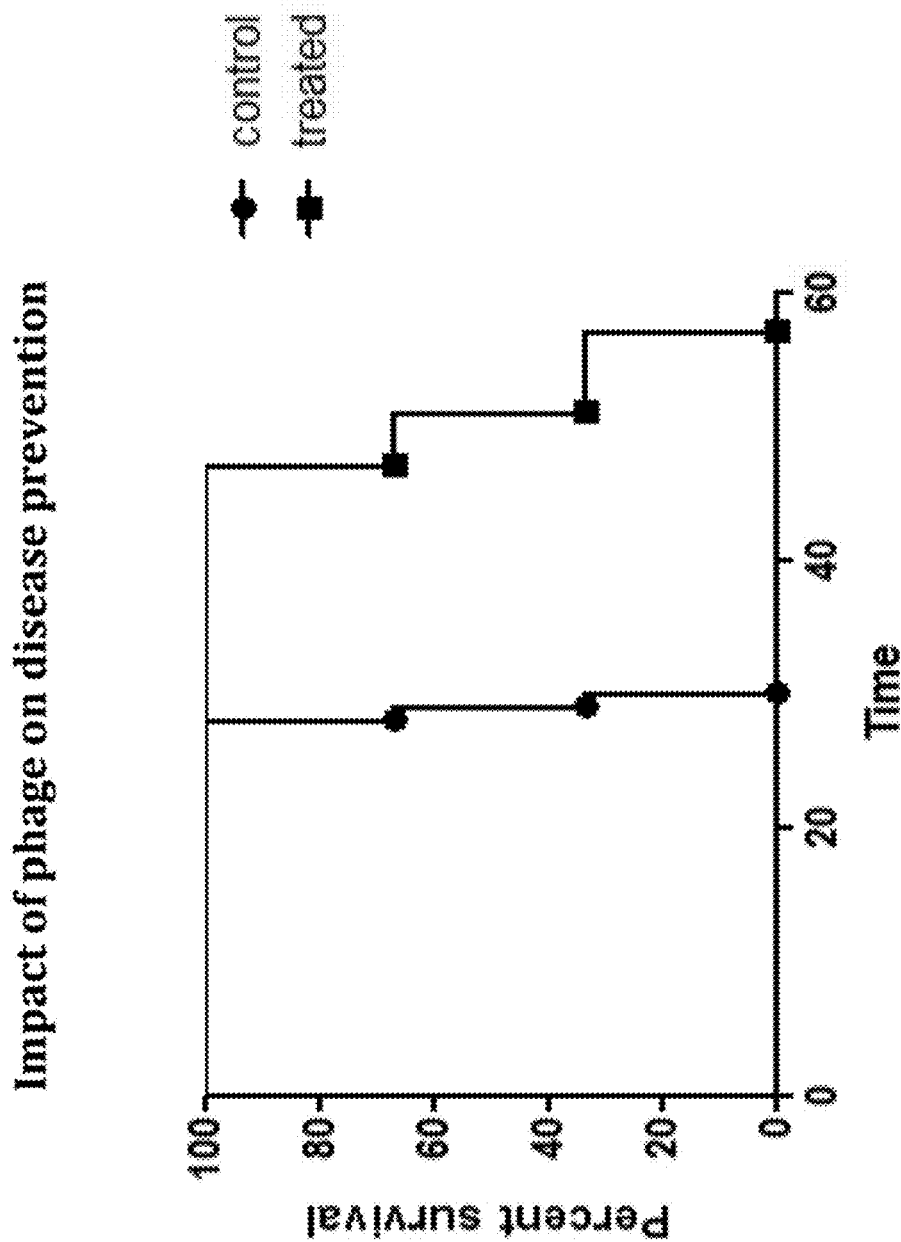
FIG. 9 shows the impact of phage and disease prevention in a severe model study when phage is administered to a hamster.

A study was undertaken using the *C difficile* toxin producing strain B1 (ribotype 031). Extensive experience with this strain has revealed 100% fatal infection approximately 28-33 h post infection (ref Goulding 2009). In this experiment, Six animals were treated orally with clindamycin and 24 h later infected with 5000 spores of *C. difficile* B1. To reduce stomach acidity prior to treatment with phage all animals were dosed with sodium bicarbonate 30 mins before treatment with bacteriophage CD-HM1 ($10^8$ pfu/dose). Control animals were mock treated with phage diluents alone. Treatment with CD-HM1 began at the point of infection and continued every 8 h until experimental clinical endpoint. Control animals developed diarrhoea approximately 26 h post infection and were culled at clinical endpoint at around 30 h. In contrast, treated animals remained symptom free for 38 h and finally succumbed to fatal infection some 50 h post infection (p=0.0075). Results are found in FIG. 9.

8. Multi-Phage Preparation

Two bacteriophage of the Siphoviridae family CD-HS1 (also referred to as AIU-PhiX2) and AIU-ST, were selected as phage known to infect *C. difficile* strains of the epidemically important ribotype 027. In particular, both phage have been used to infect AIU, a nosocomial strain of a ribotype 027. An exponentially growing culture of AIU was infected at OD 0.2 (550 nm) with a mixture of the two bacteriophages at an MOI (Multiplicity of Infection) of 10. The two phages were also individually used at the same MOI to infect separate cultures of AIU. The culture medium (BHI) was used as control.

Figure 10:
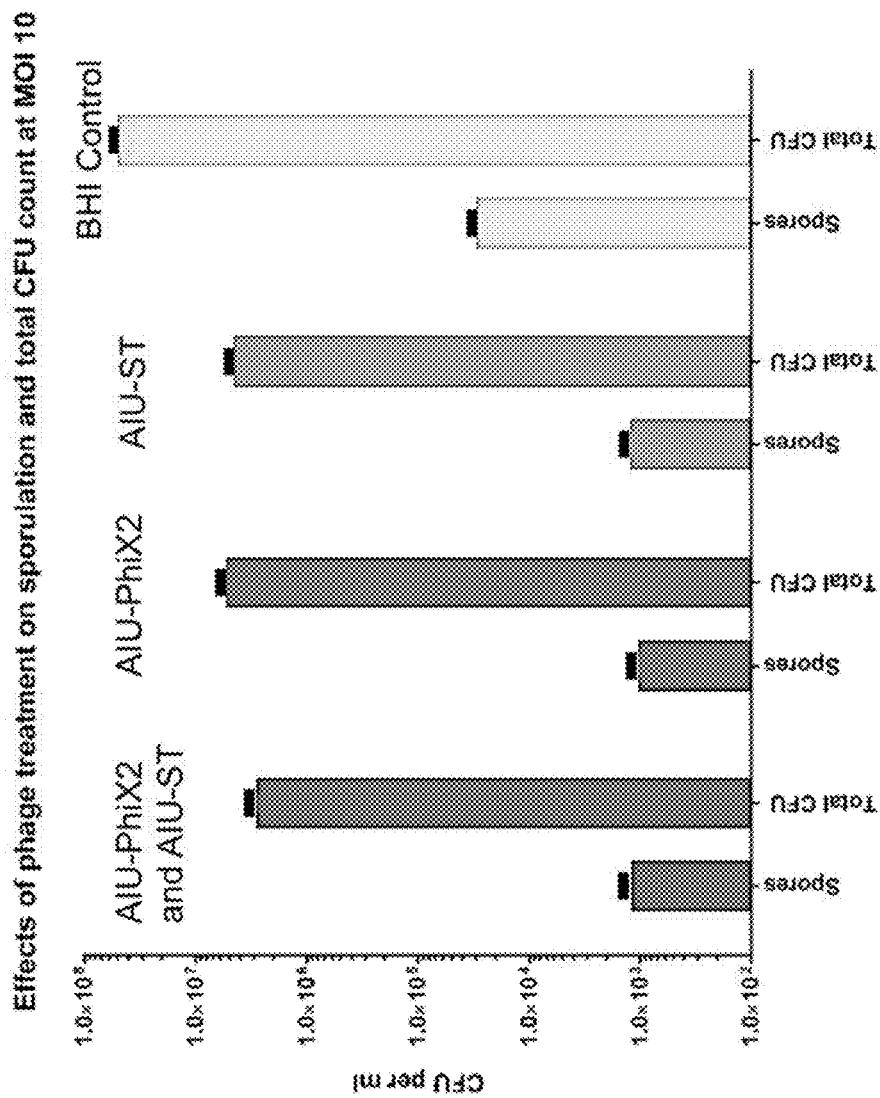
FIG. 10 shows the effect of phage treatment comprising the use of two phages on the sporulation and on the total CFU count for C ribotype 027.

Each of the cultures were incubated for 24 hours and the cells were harvested by centrifugation at 4000 g. The supernatant was decanted and the pellets were suspended in BHI. One half of the resuspensions was used to determine the total CFU count by plating while the other half was first heated at 60° C. for 20 minutes to kill all the vegetative cells and then plated in order to determine spore counts. All the counts were taken on plates with CCEY agar which allows *C. difficile* spores to grow. After 24 hours incubation in the anaerobic cabinet the total CFU and spore counts were enumerated and the results are shown in FIG. 10.

The results showed that the bacteriophage infected cultures had reduced total *C. difficile* CFU (Colony Forming Units) and spore count compared to the control. Additionally, it was found that the simultaneous use of two phages did not lower the effect of using one phage alone, thereby demonstrating that that the two different phages do not inhibit each other.

9. Phage Therapy on *C. difficile* Infection in HT29 Cells

In order to determine the effect of CD-HS1 on *C. difficile* ribotype 027 infected human epithelial cell-line HT29 cells, HT29 cells were cultured at 37° C., in a 5% carbon dioxide ($CO_2$) humidified incubator in growth medium consisting of Dulbecco's modified Eagle's medium (DMEM, Sigma) supplemented with 10% heat inactivated bovine serum (FBS, Invitrogen), antibiotics (penicillin/streptomycin, Sigma) and L-glutamine. HT29 cells were received in a small 25 cm2 tissue culture flask from Glasgow University from which stocks were prepared, cryopreserved and stored in a vapour phase liquid nitrogen dewar (Taylor-Wharton) until required. All cell culture work was carried out in a class II biological safety cabinet (Faster) using aseptic techniques. Cells were cultured until confluent in tissue culture flasks. The growth medium was removed by gentle pouring and the cells gently washed in 25 ml of warm Dulbecco's phosphate-buffered saline (DPBS, Oxoid). 3 ml of Trypsin-EDTA solution (Sigma) was added to the flask to cover the monolayer after pouring off the DPBS. The flask was then incubated at 37° C. for 1 to 2 minutes and the cells washed with pre-warmed growth medium and centrifuged at 500×g for 3 minutes. The supernatant was removed and the pellet of HT29 cells was used for one of the following: sub-culturing, cryopreservation or investigation of the cytotoxicity effects of *C. difficile* on HT29 cells in the presence and absence of phage.

$2 \times 10^6$ cells/ml of HT29 cells were aliquoted into 0.5 ml volumes in cryovials (Nalgene) and 0.5 ml of cryoprotectant was added. The vials were stored at −70° C. in a vapour phase liquid nitrogen dewar (Taylor-Wharton) until required.

Culturing HT29 Cells for Determining Cytotoxicity Effects.

Figure 11:
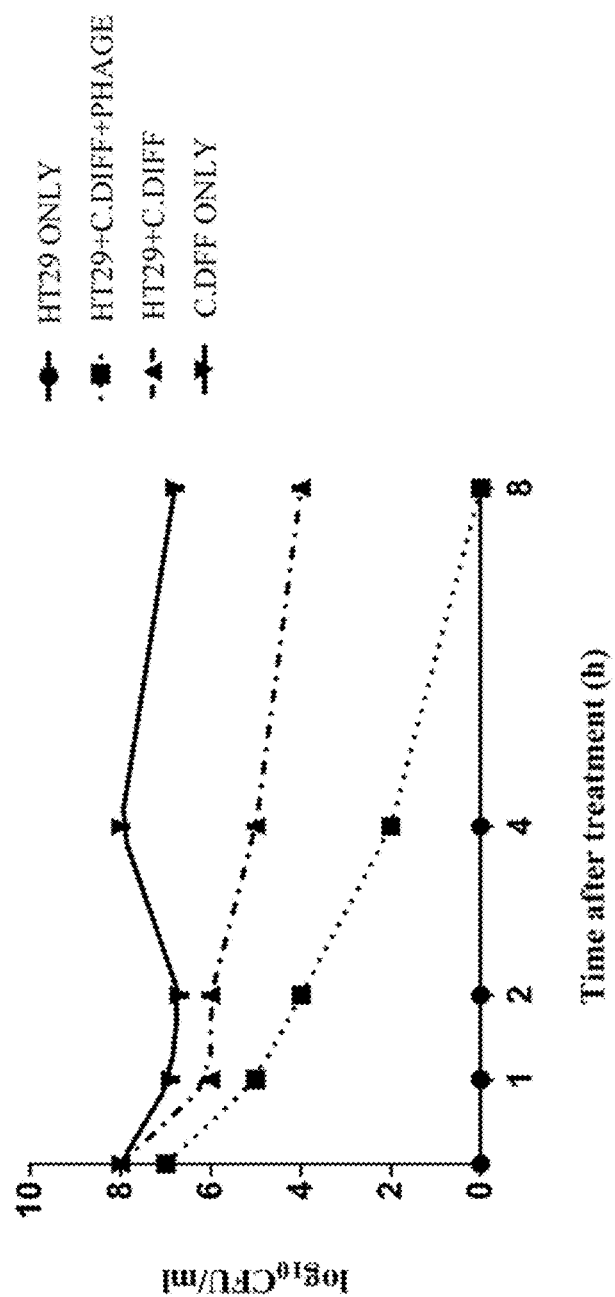
FIG. 11 shows the number of viable *C. difficile* cells following phage treatment of *C. difficile* infected HT29 cells.

$5 \times 10^4$ cells/ml of HT29 cells were seeded into a 24 well microtiter plate and incubated at 37° C., 5% CO2 humidified incubator until confluent. The cells were then used for assessing the effects of *C. difficile*, phage, and phage-infected *C. difficile* culture on HT29 cells. The HT29 cells were infected with *C. difficile* ribotype 027. Enumeration of viable *C. difficile* in the culture medium was determined by spot testing at 4 time points (ie 1 hour after treatment, 2 hours after treatment, 4 hours after treatment and 8 hours after treatment). This study was carried out in the absence or presence of infection of the *C. difficile* with the aforementioned phage. As a control, the study was carried out in the absence of *C. difficile* infection and phage, ie uninfected HT29 cells were grown in the culture media. The mean values for the three biological replicates for each of the above surveys are presented in FIG. 11. During the course of treatment, the number of viable *C. difficile* in the phage treated *C. difficile* infected HT29 cells reduced from $8.9 \times 10^6$ CFU/ml to almost all bacterial cells dying 8 hours after infection. However, in the non-phage treated infected HT29 cells, $8 \times 10^3$ CFU/ml of *C. difficile* remained viable after 8 hours, demonstrating that phage therapy of *C. difficile* infection in HT29 cells reduced the number of viable *C. difficile*.

10. The Effect of Phage Therapy on the Number of Free Phage

Figure 12:
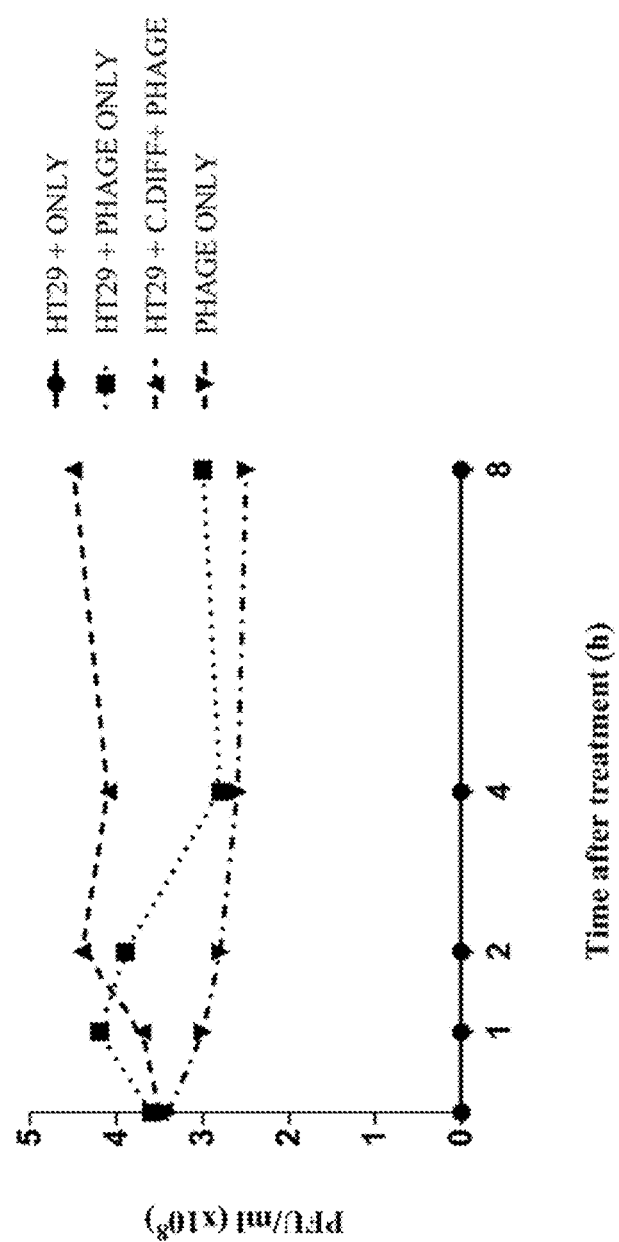
FIG. 12 shows the number of free phage following phage treatment of *C. difficile* infected HT29 cells.

Clearly, phage need to be able to replicate if they are to spread through the gut environment and clear an infection. To determine their ability to replicate, the number of free phage following phage therapy of *C. difficile* infection in HT29 cells were enumerated by spot tests and plaque assays and are shown in FIG. 12.

Phage therapy of *C. difficile* infection in HT29 cells (FIG. 12) resulted in an increase in the number of free phages (PFU), with phage bursts occurring 2 hours after treatment compared to phage treated un-infected HT29 cells. This observation demonstrates the successful replication of phage within *C. difficile* when they are grown on epithelial cells.

Figure 13:
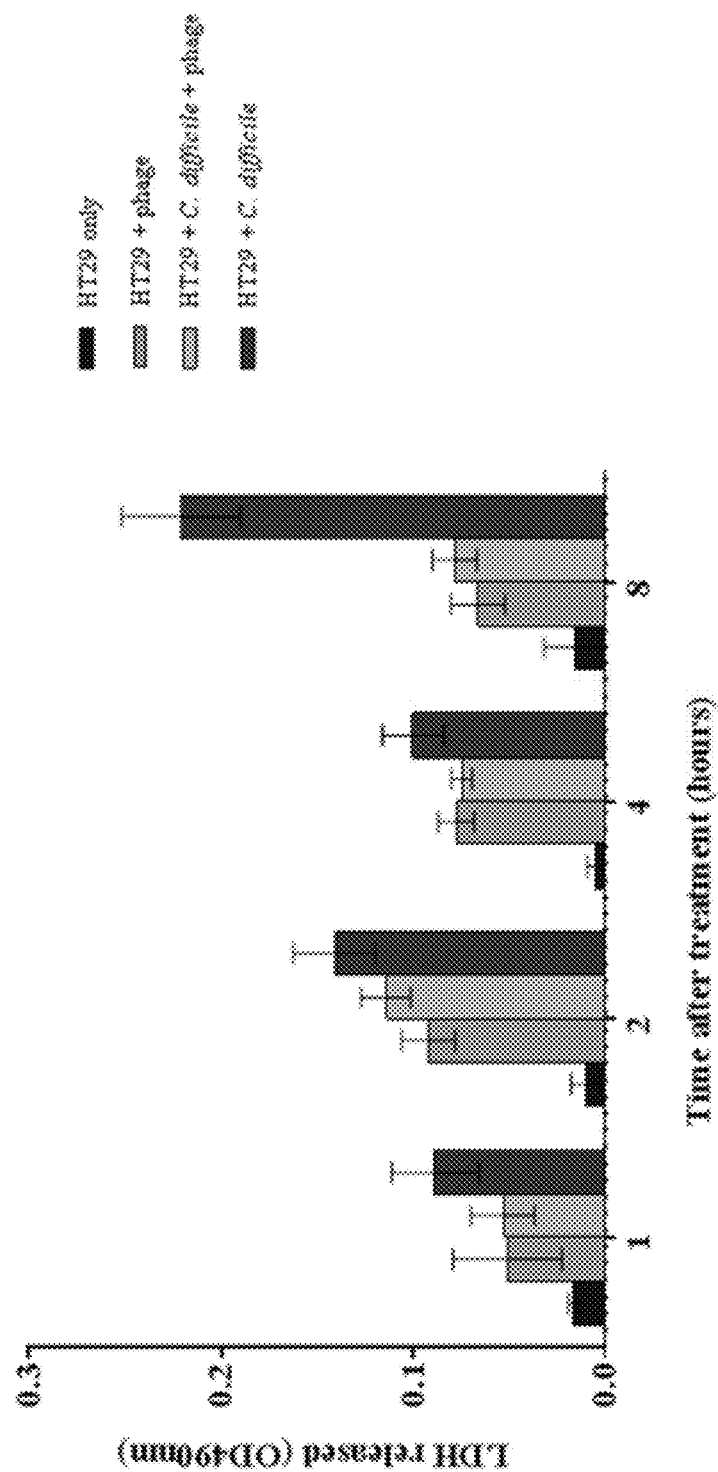
FIG. 13 shows the cytotoxicity effect following phage treatment of *C. difficile* infected HT29 cells. The amount of cytosolic LDH released into the culture medium by *C. difficile* infected HT29 cells is plotted along the Y-axis.

11. The Effect of Phage Therapy on Lactate Dehydrogenase Release from HT29 Cells In order to determine the loss of membrane integrity of HT29 cells and thus the level of cytotoxicity, the amount of cytosolic lactate dehydrogenase (LDH) released into the culture medium by *C. difficile* infected HT29 cells in the presence and absence of phage was assessed and is shown in FIG. 13.

A commercial cytotoxicity kit (Promega, CytoTox 96) was used to determine the amount of LDH released by HT29 cells into the culture medium in the presence and absence of phage over a time course of 8 hours. Mean values of three biological replicates consisting of three technical repeats are presented. Error bars denote standard error of the mean. Background values from BHI and growth media were subtracted from each result.

The amount of LDH released from *C. difficile* infected HT29 cells was significantly higher at 8 hours compared to phage-treated *C. difficile* infected HT29 cells for the same time period ($P<0.0001$). Phage treatment therefore, reduced the cytotoxicity effect caused by *C. difficile* infection in HT29 cells and no significant levels of toxin were released.

The invention claimed is:

1. A method of treatment comprising administering to a patient a pharmaceutical composition comprising two or more bacteriophages selected from the group consisting of NCTC 12081404, NCTC 12081405, NCTC 12081406, NCTC 12081407, NCTC 12081408, NCTC 12081409, and NCTC 12081410, wherein the two or more bacteriophages are capable of lysing more than 5 different ribotypes of *Clostridium difficile*, and wherein the 5 different ribotypes comprise 014/20 or 027.

2. The method of claim 1, wherein the method is for treating *Clostridium difficile* infection.

3. The method of claim 2, wherein the infection presents as any condition selected from the group consisting of diarrhoea, colitis, sepsis, toxic mega colon, hypotension, gasteroenteral perforation, *Clostridium difficile* associated disease, and combinations thereof.

4. The method of claim 1, wherein the method is for prophylactic treatment.

5. The method of claim 4, wherein the method comprises administering the panel of bacteriophages to a subject that has not yet been colonized by *Clostridium difficile*, or a subject that has been colonized by *Clostridium difficile* but colonization has not progressed to infection.

6. A method of treating *Clostridium difficile* infection comprising administering a therapeutically effective amount of a pharmaceutical composition to a subject to be treated for *Clostridium difficile* infection, wherein the pharmaceutical composition comprises two or more bacteriophages selected from the group consisting of NCTC 12081404, NCTC 12081405, NCTC 12081406, NCTC 12081407, NCTC 12081408, NCTC 12081409 and NCTC 12081410, wherein the two or more bacteriophages are capable of lysing more than 5 different ribotypes of *Clostridium difficile*, and wherein the 5 different ribotypes comprise 014/20 or 027.

7. The method as claimed in claim 6, wherein the infection presents as any condition selected from the group consisting of diarrhoea, colitis, sepsis, toxic megacolon, hypotension, gasteroenteral perforation, and *Clostridium difficile* associated disease.

8. A method of prophylactic treatment comprising administering a therapeutically effective amount of a pharmaceutical composition to a subject that has not yet been colonized by *Clostridium difficile*, or a subject that has been colonized by *Clostridium difficile* but the colonization has not progressed to infection, wherein the pharmaceutical composition comprises any two or more bacteriophages selected from the group consisting of: NCTC 12081404, NCTC 12081405, NCTC 12081406, NCTC 12081407, NCTC 12081408, NCTC 12081409, and NCTC 12081410, wherein the two or more bacteriophages are capable of lysing more than 5 different ribotypes of *Clostridium difficile*, and wherein the 5 different types of ribotypes comprise 014/20 or 027.

\* \* \* \* \*